United States Patent
Levetan

(10) Patent No.: US 8,808,689 B1
(45) Date of Patent: Aug. 19, 2014

(54) INSULIN INDEPENDENCE AMONG PATIENTS WITH DIABETES UTILIZING A PPI IN COMBINATION WITH AN IMMUNE TOLERANCE AGENT

(71) Applicant: Claresa Levetan, Bryn Mawr, PA (US)

(72) Inventor: Claresa Levetan, Bryn Mawr, PA (US)

(73) Assignee: Perle Bioscience, Inc., Atlanta, GA (US)

( * ) Notice: Subject to any disclaimer, the term of this patent is extended or adjusted under 35 U.S.C. 154(b) by 0 days.

(21) Appl. No.: 13/768,472

(22) Filed: Feb. 15, 2013

Related U.S. Application Data

(63) Continuation-in-part of application No. 13/662,209, filed on Oct. 26, 2012, and a continuation-in-part of application No. 13/662,232, filed on Oct. 26, 2012, and a continuation-in-part of application No. 13/662,245, filed on Oct. 26, 2012, and a continuation-in-part of application No. 13/662,253, filed on Oct. 26, 2012.

(60) Provisional application No. 61/749,197, filed on Jan. 4, 2013, provisional application No. 61/706,225, filed on Sep. 27, 2012.

(51) Int. Cl.
*A01N 63/00* (2006.01)
*C12N 5/00* (2006.01)
*A61K 35/407* (2006.01)

(52) U.S. Cl.
CPC .................................. *A61K 35/407* (2013.01)
USPC ......................................... 424/93.7; 435/325

(58) Field of Classification Search
USPC .......................................... 424/93.7; 435/325
See application file for complete search history.

(56) References Cited

U.S. PATENT DOCUMENTS

| 7,393,919 B2 * | 7/2008 | Levetan et al. ................. 530/327 |
| 2009/0054314 A1 * | 2/2009 | Cruz ................................ 514/12 |

OTHER PUBLICATIONS

Noguchi et al. (Immunosuppression for Islet Transplantation. Acta Med. Okayama 2006 60(2):71-76).*

* cited by examiner

*Primary Examiner* — Karen Cochrane Carlson
*Assistant Examiner* — Natalie Moss
(74) *Attorney, Agent, or Firm* — James A. Italia; Italia IP

(57) ABSTRACT

To date, no immune tolerance agent or combination of immune tolerance agents has been able to sustain insulin-independence among type 1 diabetes patients. This patent provides methods and pharmaceutical compositions for providing insulin independence among newly diagnosed and existing type 1 diabetes. Methods include utilization of PPIs, which increase gastrin resulting in the transformation of human ductal tissue into insulin-secreting new beta cells, used in combination with an immune tolerance agent to protect the new insulin-producing beta cells generated by the PPI from immune destruction. Compositions and methods are provided for beta cell generation therapy comprising at least one member from a group of PPIs with formulations selected from immune tolerance agents, when used in combination result in insulin-independence among new and existing type 1 patients whom currently require insulin to sustain life. Compositions and methods are provided for insulin-independence among type 2 patients using PPIs when combined with therapeutic agents utilized for the treatment of type 2 diabetes.

14 Claims, 11 Drawing Sheets

Combination immune-based therapies for type 1 diabetes

| Combination | | Commentary on: | |
|---|---|---|---|
| Drug no. 1 | Drug no. 2 | Evidence for tolerance and other (dis)advantages | Drug availability |
| Anti-CD3 •Teplizumab (MacroGenics/Eli Lilly) •Otelixizumab (TolerX/GSK) | Antigen •Oral insulin •GAD-Alum (Diamyd) •Proinsulin DNA (BHT-3021, Genentech) •Proinsulin peptide | –Extended benefit of anti-CD3 monotherapy in Phase II –Long-term induction of Tregs by anti-CD3 in preclinical models –Synergy of anti-CD3 and antigen demonstrated in preclinical models –Antigen-specific suppression shown in preclinical models for antigens | Availability will require negotiations between companies |
| T cell modulation (anti-CD3) •Teplizumab (MacroGenics/Eli Lilly) •Otelixizumab (TolerX/GSK) | Anti-inflammatory •IL-1RA Anakinra (Amgen) •IL-1 Trap Rilonacept (Regeneron) | –See above | Availability will require negotiations between companies |
| B cell depletion (anti-CD20) •Rituximab (Genentech) | Antigen •oral insulin •GAD-Alum (Diamyd) •Proinsulin DNA (BHT-3021, Genentech) •Proinsulin peptide | –Clinical and preclinical studies on all agents show potential effects as monotherapies (and for antigens see above) | Availability will require negotiations between companies |
| Immune depletion/modulation •Anti-thymocyte globulin (ATG; thymoglobulin, Genzyme) | Immune modulation •GM-CSF (Neulasta, Amgen) | –Encouraging preclinical results of combination in NOD mice | Good for all agents |
| Antigen •GAD-Alum (Diamyd) | Antigen •Oral insulin •Proinsulin DNA •Proinsulin peptide | –Encouraging preclinical results of antigen combinations in NOD mice – Induction of Tregs across diverse genetic backgrounds –Specific combinations not tested preclinically or clinically | All early development phase and will therefore require negotiation |
| T cell modulation (anti-CD3) •See above | Incretin mimetic •Exendin-4 (Exenatide, Amylin/Lilly) | –Efficacy of combination in animal models | Availability will require negotiations between companies |
| T cell modulation (anti-CD3) or B cell depletion (anti-CD20) | Anti-inflammatory •Anti-TNF-α (Enbrel, Amgen) | –All agents show success in monotherapy trials and target different pathways – No data on combinations in preclinical setting | Availability will require negotiations between companies |
| Other possible combinations with minimal supporting data: | | | |
| Anti-inflammatory • e.g. see above or • anti-IL-6 (Tocilizumab, Roche) | Antigen | | |
| B cell depletion (anti-CD20) | IL-2 pathway blockade • Rapamycin (Rapamune, Wyeth) | | |
| B cell depletion (anti-CD20) | Incretin mimetic | | |
| B cell depletion (anti-CD20) | Anti-inflammatory | | |
| T cell modulation (anti-CD3) | Anti-inflammatory • α-1 anti-trypsin (Aralast, Baxter) | | |
| Immune modulation • Anti-IL-12/23 (Stelara, J&J) | Antigen | | |
| Antigen • CTB-Ins plasmid | Antigen | | |
| Antigen • CTB-Ins plasmid | Immune modulation • IL-10 plasmid | | |

Fig. 1

Human Ductal Transformation to Islets in Presence of Regeneration Agent
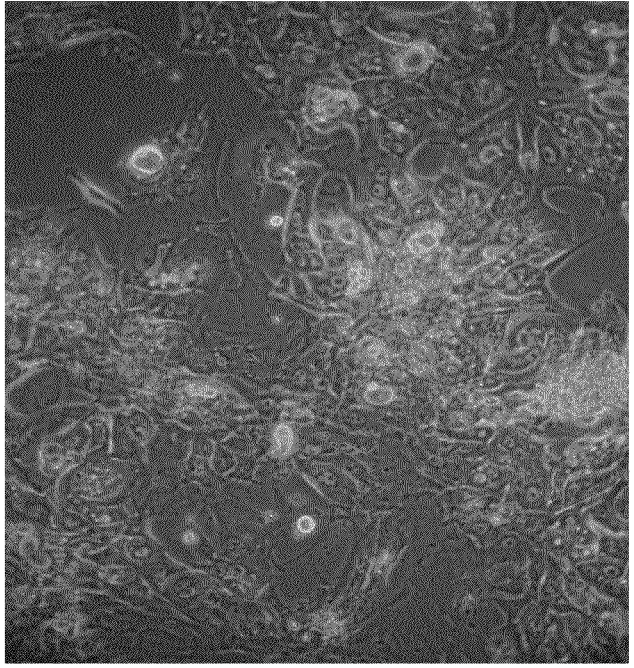
Transformation of Human Ductal Tissue into Islets staining for Insulin, Glucagon and Somatostatin in the presence of a Regeneration Agent.
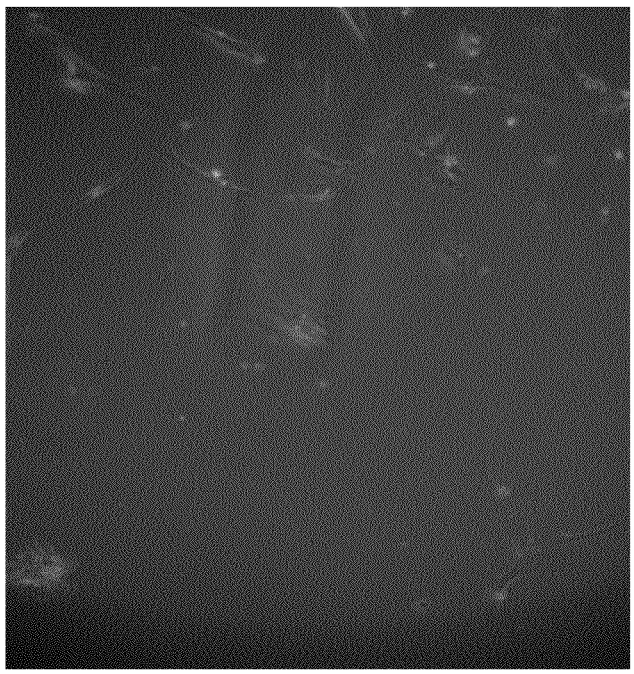
Human Ductal Tissue separated From Islets
Fig. 2

Lansoprazole

Cyclosporine

Pharmaceutical Composition of Cyclosporine and Lansoprazole

INSULIN INDEPENDENCE AMONG PATIENTS WITH DIABETES UTILIZING A PPI IN COMBINATION WITH AN IMMUNE TOLERANCE AGENT

CROSS-REFERENCE TO RELATED APPLICATIONS

This application claims the benefit of priority to U.S. Provisional Application Ser. No. 61/706,225 filed Sep. 27, 2012 and U.S. Provisional Application Ser. No. 61/749,197 filed Jan. 4, 2013. This application is also a Continuation-In-Part of U.S. Non-Provisional application Ser. Nos. 13/662,209, 13/662,232, 13/662,245, and 13/662,253 all of which were filed on Oct. 26, 2012 and the disclosures of which are incorporated by this reference.

FIELD OF THE INVENTION

The present invention relates to novel therapies, pharmaceutical compositions and methods for treating conditions that are associated with or are a risk factor for impaired glucose homeostasis utilizing a proton pump inhibitor alone or in combination with an immune tolerance agent. To date, there has not been any human clinical trials utilizing both an immune tolerance agent and an agent that regenerates beta cells. This invention provides for novel methods and pharmaceutical compositions to provide insulin independence among patients with type 1 and 2 diabetes.

BACKGROUND OF THE INVENTION

Diabetes is one of the most serious health issues facing humanity with The World Health Organization reporting that approximately 346 million people worldwide have already been diagnosed with diabetes, making it a global challenge. Despite all of the new technologies and therapies diabetes remains the leading cause of blindness, amputations and kidney failure necessitating dialysis.

In the US alone, there are 23 million Americans with diabetes having a financial burden of $174 billion a year, which is as much as the costs of the conflicts in Iraq, Afghanistan and the global war on terrorism combined. Diabetes costs the US more than the $150 billion in damage caused by Hurricane Katrina. There are one million new cases of diabetes per year in the United States.

Current therapies for diabetes do no reverse the underlying mechanism of disease, which is a lack of beta cells that make insulin. Despite many well-intended lifestyle interventions and studies including the TODAY Study among children and adolescents diagnosed with diabetes, over time insulin is still required by most patients because at the time of diagnosis there is already a reduction in 90% and 50-75% of the beta cell mass in patients with type 1 and type 2 diabetes, respectively. None of the current therapies significantly increase beta cell mass.

Research carried out over the past century has more clearly found that generating new beta cells that make insulin is the key to reversing this disease. This invention specifically provides for novel methods and pharmaceutical compositions that have not been previously discussed or written about, other than by this inventor. The ability to transform extra-islet pancreatic tissue into new islets is a very new area of study.

The ability to transform ducts to islets is a new concept that is still questioned by many. For example, in mouse models, Melton and colleagues demonstrated that new beta cells arise only from existing beta cells and not from ductal progenitors in mice and this work has been central in the thinking among most in the field. Dor Y et al. 2004 Nature 429, 41-6.

In contrast, work by this inventor demonstrates clear and distinct differences between the islets of Langerhans in man and mouse and how new islets can and are formed from ductal progenitors in certain instances and by certain regenerative gene proteins and hormones in man but not in mice. Levetan C. 2010, J Diabetes; 2(2):76-84, Levetan C S, et al., Endocr Pract. 2008 December; 14(9):1075-83. Levetan C S and Pierce S M. Endocr Pract. 2012 Nov. 27:1-36. [Epub ahead of print]. The two clinical trials designed by this inventor utilizing an immune tolerance agent with a beta regeneration agent are the first described.

At present, the immunologists in the field of diabetes still maintain that given that diabetes is an autoimmune disease, sufficient and proper immune blockade should theoretically reverse diabetes since the mechanism of action of autoimmune destruction is blocked. This inventor contends that there is a major flaw to the current hypothesis that if immune destruction is blocked, then diabetes will be resolved.

Supporting this hypothesis that specifically posits that immune tolerance alone is not enough to reverse diabetes are human trials with immune tolerance agents given to new onset type 1 patients within the first months of diagnosis that have rendered 67.5% of patients insulin-free within 7 weeks. This efficacy can be sustained by 50% of patients after a year of therapy, but over time, all require insulin again. Bougneres P F. N Engl J. Med. 1988.17; 318(11):663-70, De Filippo G. Diabetes. 1996; 45(1):101-4. Unlike type 1 diabetes mouse models, humans have a much lower rate of beta cell turnover and immune tolerance alone in man does not provide regeneration of new beta cells to maintain insulin independence. At the time of diagnosis of type 1 diabetes, there is less than 10% of baseline beta mass remaining, and over time, without regeneration of new beta cells, there is continued apoptosis among the limited remaining beta cells.

This invention specifically provides new art that distinguishes the vast differences between the islets of Langerhans in men and mice, including the specific neuronal, vascular and cellular differences and differences in beta cell turnover rates. These differences account for why immune therapy successes in mice are not seen in men, and this invention addresses this lack of success by demonstrating that a beta regeneration agent is required with an immune tolerance agent to render humans with diabetes, insulin-free (Levetan C S Endocr Pract. 2012 Nov. 27:1-36. [Epub ahead of print]).

This inventor hypothesizes that the faster beta cell turnover rate in rodents compared to man may be due to the continuous eating patterns in rodents compared to man and also the greater percentage of beta cells compared to other cell types in rodents compared to man. This inventor explains that the success of reversing diabetes in rodents by treating NOD mice with an immune tolerance agent alone is not translated into humans because of the faster beta cell regeneration in rodents that is not seen in man. Thus, humans require both an immune tolerance agent and a beta regeneration agent for insulin independence.

Although combination therapy for type 1 diabetes has been discussed, the combination of an immune tolerance agent with a beta regeneration agent has not, nor has there been any mention of a proton pump inhibitor and an immune tolerance agent except by this inventor. For example, Matthews and colleagues recently published a paper entitled, "Developing Combination Immunotherapies for Type 1 Diabetes: Recommendations from the ITN-JDRF Type 1 Diabetes Combination Therapy Assessment Group," which provides recommendations on reversing diabetes from frog thought leaders in the field of diabetes, with the conclusions that combination therapy consists of two immune tolerance agents without any mention of use of a beta regeneration agent. Matthews J B. Clin Exp Immunol. 2010 May; 160(2): 176-184.

According to Matthews and colleagues, "With these considerations in mind, the Assessment Group listed and prioritized combination therapies with the understanding that developments in preclinical (combination safety and efficacy) testing and/or ongoing clinical trials could subsequently affect the relative ranking. The Group indicated a preference for combination therapies with anti-CD3 and either antigen (such as oral insulin, GAD alum, proinsulin peptide or proinsulin DNA) or an IL-1 pathway anti-inflammatory (such as Anakinra or Rilonacept)." Table 1 from Mathews and colleagues lists two columns of immune tolerance agents to be placed in combination with one another with no mention whatsoever for the need of a beta regeneration agent, or any other agents for the treatment of type 1 diabetes other than immune modulation agents. Matthews J B, Clin Exp Immunol. 2010 May; 160(2): 176-184. The viewpoint that combination therapy for type 1 diabetes infers the use of two immune tolerance/immunomodulatory agents in combination with one another was also the conclusion of the 2012 City of Hope Annual Rachmiel Levine Diabetes Symposium. Additionally, none of the recommendations made by the Type 1 Diabetes Combination Therapy Assessment Group, Juvenile Diabetes Research Foundation International, Immune Tolerance Network mention the usage of generalized immune tolerance agents, such as cyclosporine, which this inventor finds to be the most effective immune tolerance agent for initial remission for recent onset diabetes. The Type 1 Diabetes Combination Therapy Assessment Group, Juvenile Diabetes Research Foundation International and the Immune Tolerance Network specifically only define cure as coming from targeted immune tolerance agents with no mention of cyclosporine, proton-pump inhibitors, beta regeneration agents, which are unique and specific to this invention. Matthews J B. Clin Exp Immunol. 2010 May; 160(2): 176-184.

There has been no mention by those proposing combination therapy of using an immune tolerance agent with a regeneration agent such as gastrin, proton pump inhibitors or Reg peptides. This invention describes new methods for reversing type I diabetes in human that specifically requires both an immune tolerance agent and a beta regeneration agent, which has not been discussed or studied or written about by previous investigators in the diabetes field.

One of the reasons that reversal of diabetes is only considered possible with immune tolerance agents is that diabetes is an autoimmune disease and so many immune agents have reversed diabetes in type 1 diabetes mouse models (NOD). This inventor disagrees with the conventional thinking described by Melton and others in mice, which claim that beta regeneration is only possible from other beta cells. This inventor has demonstrated that there are different pathways in man compared to rodents as well as the ability in man to transform extra-islet ductal tissue into new islets containing new pools of beta cells. Levetan C S. Endocr Pract. 2008 December; 14(9):1075-83, Levetan C. 2010, J Diabetes; 2(2): 76-84, Levetan C S Endocr Pract. 2012 Nov. 27:1-36. [Epub ahead of print]). This invention provides methods for the treatment of diabetes wherein new islets can be formed from human ductal progenitors in the presence of a regeneration a agent such as proton pump inhibitors, which increase gastrin, resulting in the formation of new islets containing new pools of beta cells.

This inventor also shows why single therapy immune agents have been able to reverse diabetes in NOD models of type 1 diabetes in mice, but have not been able to reverse diabetes in man because a beta regeneration agent is specifically necessary in man due to the slower beta turnover rate in mice as compared to man. (Levetan C S Endocr Pract. 2012 Nov. 27:1-36. [Epub ahead of print]).

This inventor has also shown that in contrast to the many descriptions of similarities between the islets of mice and men of the past, human islets are vastly different from that of rodents in composition, architecture, innervation, and function. (Levetan C S Endocr Pract. 2012 Nov. 27:1-36. [Epub ahead of print]). Human beta cells are not clustered in the center of an islet as they are in rodents. Differing greatly from rodents, as much as 70% of human beta cells have direct physical associations with other endocrine cells (e.g., the alpha, delta, gamma/pancreatic polypeptide cells) and the greater percentage of non-beta cells in humans (Levetan C S Endocr Pract. 2012 Nov. 27:1-36. [Epub ahead of print]).

This inventor has furthermore described how human and non-human primate islets have more prominent and developed internal vasculature than rodents. Levetan C S Endocr Pract. 2012 Nov. 27:1-36. [Epub ahead of print]. The blood vessels within the human islet contain a larger proportion of smooth muscle cells, which has implications for the innervation of islets by the sympathetic nervous system fibers. Conversely, rodent islet vasculature consists mainly of endothelial tubes devoid of smooth muscle cells, and occupies a smaller physical space within the islets. Levetan C S Endocr Pract. 2012 Nov. 27:1-36. [Epub ahead of print]. Thus, sympathetic nerves may regulate the secretion of several hormones within human islets via the regulation of local blood flow, and play a greater role in human islets compared to rodents. Due to these differences, rodent models that have been successful using a sole immune tolerance agent may not apply to, and have been shown not to work in man for reversal of type 1 diabetes.

Although type 1 diabetes is an autoimmune disease, this inventor has demonstrated distinct differences and complexities in islets of humans as compared to rodents and why insulin independence requires more than a single or even multiple immune tolerance agent(s) to reverse the disease. Levetan C S Endocr Pract. 2012 Nov. 27:1-36. [Epub ahead of print].

Human islets differ in their cholinergic neuronal innervations in comparison to rodent islets, with additional evidence suggesting that there are more alpha cells than beta cells in man compared to the rodent because man is more dependent on glucagon regulation than mice. Levetan C S Endocr Pract. 2012 Nov. 27:1-36. [Epub ahead of print]. These findings are underscored in the 2012 review by Unger and Cherrington describing that the juxtaposition of the functioning beta cell is critical for the regulation of glucagon from the alpha cell, which is unique to man as compared to mice. Unger R H, Cherrington A D. J Clin Invest. 2012; 122:4-12. Man is much more dependent on other cell types than beta cells, and cannot regenerate all the cell types with an immune tolerance agent alone, as has been shown in rodents.

This inventor points out the striking differences in islet complexity of islets in man compared to mice and the importance of the alpha, delta, gamma and epsilon cells, which are present to a much smaller extent in mice, also suggesting the importance of paracrine communication and the presence of complex endocrine networks and neuronal feedback mechanisms (between the islets, the peripheral vasculature, and the central nervous system) that are necessary to narrowly maintain glycemic control in man. This islet complexity in man is not seen in rodent islets and is another reason why an immune tolerance agent alone is not enough to reverse diabetes.

This inventor specifically identifies that in humans, as compared to rodents, an immune tolerance agent(s) is/are not enough to sustain insulin independence, and specifically demonstrates, which is new to the art, that therapy with both an immune tolerance agent and a beta regeneration/islet neogenesis agent are required to sustain insulin-independence in man.

At present, islet neogenesis or beta regeneration agents have not been considered in the prior art because the concept of islet neogenesis and beta regeneration from ductal progenitors is very novel and does not fit in with the current convention that a disease like diabetes has an underlying autoimmune etiology. This inventor maintains that the past and present thinking that type 1 diabetes requires only targeted immunotherapy is incorrect, and new to the art is the concept that permanent diabetes remission requires both beta regeneration agents and autoimmune agents for insulin-independence.

The concept of using an immune tolerance agent with a regeneration agent is so new to the art because concepts of regeneration agents are new to the art and have not been considered by experts, yet, to be a possible therapy for diabetes. Prior art by this inventor has demonstrated the ability to transform human ducts to islets using Reg3a peptides, but this concept is still novel in the field of diabetes and has not yet been considered to have a role in diabetes reversal. (See U.S. Pat. Nos. 7,989,415, 7,393,919, 8,211,430, 7,714,103).

Supporting this hypothesis that a beta regeneration is required for reversal of diabetes in man, is data from twenty-five years ago by Bougneres and colleagues who reported in the New England Journal of Medicine that among forty children between the ages of 7 and 15 years of age with recent onset type 1 diabetes, 67.5% of patients were able to discontinue insulin within 48±5 days of initiation of 7.5 mg/kg/day of cyclosporine in two divided dosages. Bourgneres P F. N Engl J Med 1988; 318:663-670. By 12 months after the initiation of cyclosporine, 50% of patients remained insulin free. Over the next six years of follow-up, all of the initial cohort of patients required insulin. DiFillippo G. Diabetes 45:101-104, 1996. Over the first 4 years, the cyclosporine-treated group kept plasma C-peptide at levels twice as high as the control group (P<0.02) indicating that an immune tolerance agent plays a key role in diabetes reversal, but could not sustain the insulin-free state over time because there was no beta regeneration as indicated by the loss of C-peptide over time down to the levels of the insulin-requiring control group. After four years, there were no significant differences between the group treated with cyclosporine and the control group.

Other studies have found similar data that cyclosporine had a positive impact on recent onset type 1 diabetes patients, but over time, all patients required insulin. (The Canadian-European Randomized Control Trial Group. Diabetes 1988; 37:1574-82, Assan R. Diabetes Metab Res Rev 2002; 18:464-472, Feutren G. Lancet, 1986, 19; 2(8499):119-24).

The data on cyclosporine clearly demonstrate the efficacy of an immune tolerance agent for non-sustained remission of type 1 diabetes. However, the conclusion by the authors of the cyclosporin trials was that the risks outweighed the benefits for use of cyclosporine for type 1 diabetes due to lack of any sustained remission. This inventor disagrees with the convention of current expert panels in type 1 diabetes that have considered that cyclosporine no longer plays any role today or in the future for type 1 diabetes. Matthews J B. Clin Exp Immunol. 2010 May; 160(2): 176-184. Trials with cyclosporine fell out of favor because there were no permanent remissions over time. Additionally, over the past two decades, consensus groups including the Type 1 Diabetes Combination Therapy Assessment Group, Juvenile Diabetes Research Foundation and the International, Immune Tolerance Network, has specifically not mentioned any role for regeneration agents such as gastrin, PPI, or Reg peptides nor have these groups stated that there is any role for cyclosporine in type 1 diabetes.

Lack of permanent remission is hypothesized by this inventor as to why cyclosporine has been discarded as an appropriate agent for immune tolerance type 1 diabetes. Over the past two decades, many "targeted immune therapies" have been used for reversal of diabetes and shown to be successful in reversing diabetes in rodents, but have not proved successful in man. This inventor finds that none of the targeted immune agents have shown the success of cyclosporine. Despite the usage among recent onset type 1 diabetes patients, of more than twenty different immune agents over the past two decades utilized for protecting the remaining beta cells from further autoimmune attack, there has been not been the success seen in reversing diabetes as seen in rodents because there is no ability to sustain the remaining beta cells. It is estimated that fewer than 10% of functioning beta cells remain at the time of diagnosis of type 1 diabetes. This inventor specifically finds that a general immune therapy such as cyclosporine may be the preferred agent to targeted immune therapy because of the significant ability to render up to 67.5% of recent onset patients insulin-free, which has not been seen with any of the targeted immune therapy agents. Bourgneres P F. N Engl J Med 1988; 318:663-670).

Despite trials showing a positive impact of many autoimmune therapies initiated within twelve weeks of symptoms and diagnosis of type 1 diabetes, none have resulted in lasting insulin independence nor have any come close to the insulin-free rates of cyclosporine. Immune tolerance agents utilized among recent onset type 1 patients that have shown a potential immune benefit but have not resulted in significant or sustained insulin independence include, but are not limited to the heat shock protein 60, Diapep 277, Bacille Calmette-Guérin (also known as the BCG vaccine and commonly known as the vaccine against tuberculosis), mycophenolate mofetil, daclizumab, rituximab (anti CD20), anti CD3 antibodies including hOKT3 gamma1 (Ala-Ala), and the monoclonal antibody TRX4 (ChAglyCD3), CTLA4-Ig (abatacept) a selective co-stimulation modulator as it inhibits the co-stimulation of T cells, campath-1H, anti-CD52 antibody, a humanized monoclonal antibody to T-cells, polyclonal anti-T-lymphocyte globulin (ATG), GAD antibody vaccine based on the 65 kDa isoform of the recombinant human glutamic acid decarboxylase protein (rhGAD65), diazoxide and Alpha-1 Antitrypsin. This inventor specifically identifies cyclosporine as the best agent for initial remission for type 1 diabetes and methods of this invention demonstrate that the combination of cyclosporine and a proton-pump inhibitor (PPI) result in insulin independence among new onset and existing type 1 diabetes.

This invention contradicts the recent consensus panels (Type 1 Diabetes Combination Therapy Assessment Group, Juvenile Diabetes Research Foundation International, Immune Tolerance Network) recommendations that propose that diabetes can only be reversed with a combination of two targeted immune tolerance agents. Whereas, this invention specifically claims that the general immune tolerance agent cyclosporine is the best agent when combined with a PPI and/or other islet neogenesis agents for initial insulin independence among recent onset and existing type 1 diabetes. Because diabetes is considered an autoimmune disease, the diabetes community has yet to consider that combination therapy for reversal of type 1 diabetes could be defined as being a combination of an immune inhibitor and a beta regeneration agent.

New to the art is the potential reconsideration to use gastrin for new islet formation. Human trials conducted among type 1 patients reported promising results, although the results could not be sustained, likely due to lack of usage of an immunoprotective agent. Human clinical trials with gastrin and epidermal growth factor demonstrated reductions in daily insulin requirements by much as 75% within 3 months following four weeks of therapy among existing type 1 diabetes patients (Transition Therapeutics, Mar. 5, 2007). Lack of the ability to sustain these results was likely due to the ongoing autoimmune attack on the new beta cells generated by therapy.

Gastrin alone has been shown to induce beta cell neogenesis from human pancreatic ductal tissue without epidermal growth factor in in vitro studies (Suarez-Pinzon W L et al. JCEM. 2005; 90(6):3401-3409). Humans clinical trials with gastrin have not continued because the early success that was observed was not sustained, which this inventor posits was due to lack of an immune tolerance agent to protect the newly formed islets. Supporting this hypothesis is data by J J Meier and colleagues that demonstrates that the newest generated beta cells are the cells most vulnerable to autoimmune attack. Meier J J. Diabetologia 2006, 49: 83-89.

This inventor also disagrees with the current convention that proton pump inhibitors do not play a role in the diabetes armamentarium. This invention specifically provides methods for usage of proton pump inhibitors for insulin independence in type 1 and 2 diabetes and for usage in type 2 diabetes and PreDiabetes by the mechanism of action of increasing gastrin levels.

Among the gastrointestinal hormones demonstrated to result in new beta cell formation is gastrin, which was first described in the process of transforming human exocrine tissue to human endocrine tissue by Zollinger and Ellison in 1955. Zollinger R M and Ellison E H, Ann Surg. 1955; 142(4):709-28. Administration of gastrin has been shown both in rodents and humans to stimulate beta cell neogenesis and expansion of the beta cell mass in rodents. Suarez-Pinzon W L et al J Clin Endocrinol Metab 2005; 90:3401-3409, Rooman I, et al. Diabetes 2002; 51:686-690, Wang T C. J Clin Invest. 1993; 92(3):1349-56. A human clinical trial among patients type 1 diabetes using a combination of growth factors, including the direct usage of gastrin resulted in as much as a 75% reduction in insulin requirements at four weeks among type 1 diabetes patients.

Many other groups have also demonstrated the role of gastrin in increasing beta cell mass. For example, Rooman and colleagues found a doubling beta cell mass after infusion of gastrin in rats. Rooman I et al., Diabetes. 2002; 51(3):686-90. Other research teams have shown reversal of diabetes using gastrin with other growth factors including epidermal growth factor to expand the beta cell mass in rodent models. Yu H et al., Am J Med. Sci. 2011[Epub ahead of print], Suarez-Pinzon W L, Transplant Proc. 2008; 40(2):529-32, Suarez-Pinzon W L. Diabetes. 2005; 54(9):2596-601, Brand S J, Pharmacol Toxicol. 2002 December; 91(6):414-20.

Despite very promising data at 4 weeks utilizing gastrin in patients with type 1 diabetes, without the usage of an immune tolerance agent combined with any such agent that can increase beta regeneration, an improved impact on insulin requirements is not likely to be sustained. Data from J J Meier and colleagues demonstrates that the newest beta cells are the ones that are most vulnerable to cytokine-induced death and trigger autoimmune attack. Meier J J et al Diabetologia 2006; 49(1):83-9.

Despite early findings of patients with type 1 diabetes demonstrating a significant reduction in insulin requirements and improvements in hemoglobin A1C in just four weeks, sustained results have not been seen and clinical trials have been abandoned. This inventor hypothesizes that without an immune tolerance agent to protect newly formed beta cells, autoimmune destruction limits any ability for sustained insulin independence. Similar to the great success seen among many immune tolerance agents utilized among recent onset type 1 patients, without new beta cell formation over time, the limited amount (fewer than 10%) of beta cells remaining at the time of type 1 diagnosis will undergo apoptosis until patients require insulin again. Clinical trials using gastrin alone have been terminated due to lack of sustained efficacy among patients with existing type 1 diabetes. Thus, it is critical to have an immune agent on board at the time that new beta cells are being generated.

Proton pump inhibitors (PPIs), in addition to their primary usage for reducing gastric acid, also secondarily increase gastrin. Studies conducted among patients on a high-range dosage of the PPI Lansoprazole (90 mg/day) for 6 years or greater resulted in a sustained safety profile and gastrin levels that were nearly 7-fold higher than normal. Cadiot G et al., Gastroenterol Clin Biol. 1995; 19(10):811-7. The range of normal gastrin values may vary from lab to lab with normal values that may be higher in very young children and older adults, but are generally <100 pg/mL.

Hove and colleagues in a randomized prospective clinical trial among patients with type 2 diabetes utilizing the proton pump inhibitor esomeprazole concluded that "Treatment with esomeprazole over 12 weeks did not improve insulin secretion, glycaemic control or cardiovascular disease biomarkers in patients with type 2 diabetes." Hove K D, Brøns C, Færch K, et al., Diabetologia. 2013 January; 56(1):22-30. This inventor came to a different conclusion in reviewing the data and concluded that proton pump inhibitors may play an important role in preservation of endogenous insulin secretion. Based on this inventor's conclusion, which varied markedly from that of the authors, this inventor wrote a letter to the editor of Diabetologia with a colleague stating the following:

"In the January issue of this journal Hove et al. reported that treatment with 40 mg esomeprazole over 12 weeks in patients with type 2 diabetes did not improve insulin secretion, glycaemic control or change the biomarkers of cardiovascular disease. Hove K D, Brøns C, Færch K, et al. 2013. Diabetologia 56:22-30. Here we offer a different viewpoint on the data presented by Hove et al. These authors help elucidate whether proton pump inhibitors may play a role in the diabetes armamentarium by raising gastrin levels. Gastrin was initially shown to have the potential to increase new beta cell formation by Zollinger and Ellison in 1955. Zollinger R M, Ellison (1955). E H. Ann Surg. 142:709-23."

"Hove and colleagues report a 9-fold increase in the area under the curve (AUC) of gastrin among 20 type 2 diabetes patients treated with esomeprazole, whereas patients on placebo had no significant rise in gastrin. However, based on the metabolic outcome the authors concluded that treatment with esomeprazole over 12 weeks did not improve insulin secretion or glycaemic control. We have looked at the data and found that patients in the control group had a significant 16.3% reduction (p=0.002) in AUC, whereas the esomeprazole treated patients had no decline in insulin AUC. Given the natural history of 2 diabetes characterized by the progressive loss of insulin secretion, its maintenance utilizing a proton pump inhibitor may demonstrate the potential role for such agent in the course of the disease to preserve or enhance beta cell regeneration. In this respect the effect of proton pump inhibitors might be also of interest in type 1 diabetes. Thus, previous studies utilizing gastrin and epidermal growth factor among type 1 diabetes patients found that the greatest impact was seen 1-3 months post-treatment. (Transition Therapeutics, Mar. 5, 2007)

"We believe that these results are encouraging and that further studies should be carried out to demonstrate the potential of proton pump inhibitors to preserve beta cell function. Studies among recently diagnosed type 1 diabetes patients using a proton pump inhibitor accompanied by an immune tolerance agent, could be an attractive option."

This inventor specifically identifies and defines that proton pump inhibitors may play an important role in beta regeneration by increasing gastrin levels and may therefore be utilized among both type 1 and type 2 diabetes for both preservation and regeneration of beta cells. This hypothesis is supported both by the findings of Zollinger and Ellison in 1955, which specifically demonstrate the formation of new islets by gastrin. Zollinger R M, Ellison (1955). E H. Ann Surg. 142:709-23.

This inventor also claims that PPIs can successfully be used not only in type 1 diabetes, but in type 2 diabetes. Type 2 diabetes results from a different etiology, but similar to type 1 diabetes there is a substantial loss of 50-75% of beta cell mass at the time of diagnosis; however, the loss is not as acute as that seen from the autoimmune destruction in type 1 diabetes. The beta cell loss seen in type 2 diabetes is due to a more chronic beta cell loss that is impacted by a number of factors including lifestyle, free fatty acids and genetics. Thus, while the beta call loss is not due to sudden autoimmune destruction as in type 1 diabetes, there is still the need for beta cell regeneration and sustained beta cell mass.

Among type 2 diabetes patients, there is a gradual 50-80% reduction in beta cell mass by the time of diagnosis compared to a more acute reduction in beta mass by 90% or more among type 1 patients, who commonly have an autoimmune component to their beta cell loss. Although the beta cell mass may expand several fold from birth to adulthood, this is not enough to compensate for the greater rate of beta cell loss than generation than occurs in both type 1 and 2 diabetes.

Two recent NIH studies, one in children and adolescents and the other in adults demonstrate that intensive lifestyle interventions designed to improve and impact type 2 diabetes simply have no effect in children and adolescents in glycemic control and do not limit the need for patients to move on to insulin therapy for better control of their diabetes. The TODAY Study Group. N Engl J. Med. 2012 Apr. 29. [Epub ahead of print]. Diabetes Research Program Prevention Group, Lancet. 2009; 374(9702): 1677-1686. Among children and adolescents with type 2 diabetes, therapy with metformin or lifestyle interventions did not improve diabetes control or the necessity for insulin therapy.

The TODAY study illustrates the need for new insulin-secreting beta cells to delay or prevent the adverse vascular complications of diabetes. Despite the many new treatments and technological armamentariums for diabetes, diabetes-related complications including retinopathy, blindness, neuropathy, amputations, renal insufficiency and dialysis, along with macrovascular complications including heart attack, stroke and peripheral vascular disease, continue to rise among patients with diabetes. For example, recent studies among patients with type 1 utilizing the newest technological advances including the use of glucose sensors that are located within the insulin pump that measure 288 glucose levels per day have not improved hemoglobin A1C levels as much as those seen in the DCCT trial conducted more two decades ago when sensor technology was not available and shorter acting insulin analogs were also not on the market. The DCCT Research Group. N Engl J. Med. 1993; 329(14):977-986, Bergenstal R M et al, N Engl J Med, 2010; 363(4):311-320. Bergenstal R M, et al, Diabetes Care. 2011; 34(11):2403-2405.

There is a dire need to restore new beta cells and maintain beta cell mass among type 1 and type 2 diabetes. The loss of endogenous insulin is directly correlated with a multiplicity of atherogenic risk factors for microvascular and macrovascular complications. Lack of insulin, which is the hallmark of diabetes results not only in elevated glucose levels, but also results in a large number and wide complexity of metabolic abnormalities. For example, lack of insulin results in diminished activation of lipoprotein lipase resulting in increased levels of triglyceride-rich lipoproteins including chylomicrons and very low-density lipoproteins.

The field of beta regeneration is in its infancy and the concept of a beta regeneration is still very new. This inventor has previously shown that the human Reg gene peptides are directly involved in new beta cell formation from extra-islet ductal tissue. Gastrin has also been shown to generate new islets from ductal tissue. Others have confirmed the presence of Reg in the pancreas of newly diagnosed human diabetes, with subsequent data in both human ductal tissues and from BrdU studies showing that Reg serves to directly form new beta cells from extra-islet ductal tissue, as is the case with gastrin. Levetan C S et al, Endocr Pract. 2008; 14(9):1075-1083, Rosenberg L et al, Diabetologia. 1996; 39:256-262, Li J et al, Peptides. 2009; 30(12):2242-2249, Dungan K M et al, Diabetes Metab Res Rev. 2009; 25(6):558-565. Zollinger R M, Ellison. E H. Ann Surg. 1955 October; 142(4):709-23, Wang T C, Bonner-Weir S, Oates P S et al., J Clin Invest. 1993 September; 92(3):1349-56, Wang R N, Rehfeld J F, Nielsen F C, et al., Diabetologia. 1997 August; 40(8):887-93.

Previously, this inventor demonstrated that a human Reg3a gene protein has successfully been administered to human pancreatic ductal tissue devoid of islets resulting in a significant increase in insulin concentrations indicating new beta cell formation; a 3-fold rise in total beta cells staining insulin in STZ-rendered diabetic mice was observed. Levetan C S., et al, Endocr Pract. 2008; 14(9):1075-1083. Reg3a protein and placebo-treated mice underwent an overnight fast and a fasting glucose level on the morning of day 39 of treatment. Fasting glucose levels were 258.00±84.5 mg/dl in the placebo group compared to a fasting glucose level of 111.00±11.4 mg/dL (P=0.020) in the Reg3a protein-treated mice.

To date, there has been limited awareness or acknowledgement of the Reg peptides in the diabetes community. As there are no Reg peptides on the market, this invention provides a specific and completely novel approach to the art by using a proton pump inhibitor for insulin independence, which increases gastrin levels up to 9-fold in man, along with an immune tolerance agent to protect newly formed beta cells. Hove K D, Brøns C, Færch K, et al., Diabetologia. 2013 January; 56(1):22-30.

This inventor has also investigated the role and pathways of other human hormones involved in beta cell regeneration with findings consistent with initial findings of Moore and colleagues in 1906, demonstrating the role of gastrointestinal hormones in improving diabetes control among three patients with type 1 diabetes. Levetan C. 2010, J Diabetes; 2(2):76-84, Moore et al, Biochem J. 1906; 1(1): 28-38. The mechanism of action of these gastrointestinal hormones were not only found to be in insulin secretion, but decades later these gut peptides have been shown to be involved in the transformation of extra-islet exocrine tissue into new endocrine tissue containing beta cells. Wang T C. J Clin Invest. 1993; 92(3):1349-56.

Not until 1999, when the use of cell lineage labeling became available, did the embryological concepts of the pancreas change. Whereas it had been thought that the pancreas was derived from both ectoderm and endoderm, it has now been shown that the entire pancreas arises only from endoderm during embryological development. This helps explain how beta progenitor cells have been described as residing diffusely throughout the adult pancreatic tissue and how growth factors transform pancreatic extra-islet ductal tissue into new beta cells. Over the past several decades, the ability to regenerate new beta cells from progenitor cells found within the pancreatic ductal tissue has been illustrated by many teams.

This invention provides new methods to the art of the combination of gastrin or usage of a PPI with an immune tolerance agent. The clinical trials set forth by this inventor are completely new to the art in the approach of using a beta regeneration agent with an immune tolerance agent, as well as using a general immune tolerance, cyclosporine, which has not been considered as possible therapy for diabetes for decades.

The immunosuppressive drug cyclosporine has been shown to have long-term safety and short-term efficacy for rendering new onset patients with type 1 diabetes insulin-independent. The immunosuppressive effects of cyclosporine were discovered in 1972 in a screening test on immune suppression designed and implemented by Dr. Hartmann Stähelin. The success of cyclosporine in preventing organ rejection was later shown in kidney transplants by Calne and colleagues at the University of Cambridge and in liver transplants performed initially at the University of Pittsburgh Hospital. Cyclosporine was subsequently approved for use in 1983. Since then, it has been used to prevent and treat graft-versus-host reactions in bone marrow transplantation and to prevent rejection of kidney, heart, and liver transplantation.

In addition to transplants, cyclosporine has also been used in psoriasis, severe atopic dermatitis, pyoderma gangrenosum, chronic autoimmune urticaria, and, infrequently, in rheumatoid arthritis and related diseases. It is commonly prescribed in the US as an ophthalmic emulsion for the treatment of dry eyes. Cyclosporine has also been used to help treat patients with acute severe ulcerative colitis that do not respond to treatment with steroids. This drug is also used as a treatment of posterior or intermediate uveitis with noninfective etiology. Cyclosporine is also currently used to experimentally treat cardiac hypertrophy.

To date, there have been no studies that combine an immune tolerance agent with a known beta cell regeneration growth factor that has been shown to directly stimulate the formation of new beta cells from ductal cells. The prior art in the field has described the usage of gastrin with other growth factors, but has never specifically used an immune tolerance agent in combination with these agents (See U.S. Pat. No. 6,992,060), When gastrin itself is given to type 1 patients without an agent to prevent autoimmune destruction of new beta cells, there has only been improvement over a 4-week period due to autoimmune destruction.

One of the reasons that this combination of an immune tolerance agent with gastrin or a PPI has not previously been considered and has not been obvious is because dozens of preclinical trials with rodent type 1 diabetes models including NOD mouse models have shown only the need for gastrin and other beta cell growth factors for reversal of diabetes. Likewise, rodent type 1 diabetes models including NOD mouse models have shown that using a immune tolerance agents alone is all that is needed to reverse type 1 diabetes in mice.

This inventor has shown great distinctions between the insulin-producing islets of mice and men with humans having much more complex islet structures with respect to composition of cell type, neural and vascular innervation and unique paracrine interactions that are not found in rodents. Levetan has demonstrated vast differences in the islets of mice and men, which may explain the many, many studies conducted among rodent models in the field of diabetes that later are unable to be replicated in human studies. Levetan C S et al. Endocr Pract. 2012; 27:1-36. [Epub ahead of print]. Specifically, trials with multiple different agents and types of agents have been utilized in preclinical rodent models evaluating agents that may be successful in clinical practice for usage in patients with type 1 diabetes. This inventor has also previously shown, like many other scientific teams, that after fetal development of beta cells, typically new beta cells are only derived from the existing, surviving beta cell population. Different and unique to the previous art in the field, this inventor has shown the ability to postnatally generate new beta cells by the transformation of human pancreatic ductal tissue. Levetan C. J. Diabetes. 2010; 2(2):76-84, Levetan C S. Endocr Pract. 2008; 14(9):1075-83.

New and unique research by this inventor, which has not been obvious in the prior art, is 1) the ability to reverse diabetes in the diabetic mouse models may be flawed by the complexity of the human islet compared to that of the rodent and 2) the process of generating new beta cells must be from a different source than from the beta cells remaining after the diagnosis of type 1 or type 2 diabetes is made because of the limited supply (<10% for type 1 diabetes and <50-75% for type 2 diabetes). This inventor has shown the ability to transform new pools of beta cells within new islets from extra-islet ductal tissue (See U.S. Pat. Nos. 8,211,430, 7,989,415, 7,714, 103 and 7,393,919).

There is a need in the art for new therapeutic modalities for the treatment of diabetes in humans that generate new beta cells from extra-islet tissue while preserving the population of nascent beta cells from destruction by the immune system.

BRIEF SUMMARY OF THE INVENTION

Embodiments of the present invention provide for novel therapies, pharmaceutical compositions and methods for insulin independence utilizing PPIs and immune tolerance agents in combination, which have never previously been used together for the treatment of type 1 diabetes. Methods, pharmaceutical compositions and therapies novel to the prior art are utilized to render patients with recent onset and existing type 1 diabetes insulin independent by utilizing PPIs and an immune tolerance agent. While not wishing to be bound by theory, PPIs may increase beta cell generation by their properties of increasing plasma gastrin levels as much as 9-fold, which in turn, transforms extra-islet pancreatic ductal tissue into new beta cells.

This invention identifies for the first time that the combination of therapies that includes a PPI as a beta regeneration agent in combination with an immune tolerance agent for the protection of the new beta cells generated by the PPI results in insulin-independence for patients with type 1 diabetes. The therapeutic methods described in this invention are not contained within the prior art, and specifically include, but are not limited to the usage of a PPI in combination with an immune tolerance agent, and includes the usage of cyclosporine, which has not been considered a potential agent to be used for type 1 diabetes in more than two decades with the convention being to utilize one or more targeted immune therapy(s) (FIG. 1), which have not had the impact on rendering patients insulin-free as cyclosporine has. Due to the lack of the ability to sustain the insulin-free state, over time with cyclosporine, it was given up as having a role in insulin-independence.

Whereas, this invention, finds that cyclosporine combined with a PPI may increase gastrin levels and increase The PPI increases plasma levels of gastrin, resulting in new beta cell formation, while the immune tolerance agent protects the new insulin-secreting cells from autoimmune destruction. PPIs have never been utilized with an immune tolerance agent, which this invention demonstrates is required to protect new beta cells formed by the PPI from autoimmune destruction.

This invention also provides for novel therapies, pharmaceutical compositions and methods for insulin independence among type 2 diabetes patients using PPIs alone or in combination with therapies. Although gastrin has been used alone and in combination with other growth factors in clinical trials among patients with type 1 diabetes, the combination of gastrin or usage of a PPI with an immune tolerance agent has never previously been proposed or utilized in clinical trials for type 1 diabetes patients. One of the reasons that this combination of an immune tolerance agent with gastrin or a PPI has not previously been considered is because dozens of preclinical trials with rodent type 1 diabetes models including NOD mouse models have shown only the need for gastrin and other beta cell growth factors for reversal of diabetes. Likewise, rodent type 1 diabetes models including NOD mouse models have shown that using a immune tolerance agents alone is all that is needed to reverse type 1 diabetes in mice. This inventor has shown great distinctions between the insulin-producing islets of mice and men with humans having much more complex islet structures with respect to composition of cell type, neural and vascular innervation and unique paracrine interactions that are not found in rodents.

This invention provides a new model for treatment of type 1 and 2 diabetes. Based upon the complexity and distinctions between the islets of mice and men, this invention provides for novel therapies, pharmaceutical compositions and methods for insulin independence and provides a methodology for treating patients requiring insulin that have not previously been described. The composition of a PPI and an immune tolerance agent in this invention also is used as new single product capsule and suspension.

This invention also includes methods for the treatment of type 2 diabetes, PreDiabetes or other conditions of reduced beta cells, which include the usage of a PPI in combination with another beta regeneration agent. Additionally included are in vivo methods for direct delivery of agents specified in this invention for generation of new beta cells from extra-islet ductal cells within the pancreas and provided to patients via oral delivery with and without organ specific targeting such as direct delivery to the pancreas. This invention also includes methods of ex vivo transformation of extra-islet ductal cells or pluripotent stem cells into new beta cells that are then administered to patients with new and existing type 1 and 2 diabetes, PreDiabetes or diseases of insulin deficiency, beta cell deficiency, insulin resistance and impaired glucose metabolism.

This invention includes methods for pancreatic beta cell generation and include both in vivo and ex vivo beta cell generation and methods for treating new onset and previously existing type 1 and type 2 diabetes, Latent Autoimmune Diabetes of Adulthood (LADA), those at risk for type 1 diabetes, including but not limited to those with positive autoimmune antibodies markers including Glutamic Acid Decarboxylase-65 antibody, those with PreDiabetes or diseases of hyperglycemia, glucose intolerance and beta cell impairment or deficiency, insulin resistance, associated conditions including, obesity, obesity prior to the development of diabetes, obesity in children leading to PreDiabetes, both type 1 and type 2 diabetes in childhood and adolescence and include, but are not limited to conditions such as polycystic ovarian syndrome, nonalcoholic steatohepatitis, hyperlipidemia and hypertriglyceridemia and other conditions related to the deficiency or lack of effective amounts of insulin.

This invention also describes the usage of PPI-based formulations utilized with other agents that result in new beta cell formation including, but not limited to Reg peptides, derivatives, optimized forms including peptidomimetics of the Reg peptides and stimulating antibodies to the Reg receptor and other novel agents for beta cell generation for usage in both type 1 and type 2 diabetes. Previous work by this inventor and others has shown the ability to transform human extra-pancreatic ductal tissue into new islets, which contains new beta cell populations (See U.S. Pat. Nos. 8,211,430, 7,989,415, 7,714,103 and 7,393,919).

This invention also provides for pharmaceutical compositions comprising a PPI(s), immune tolerance agent(s), and optionally, other beta regeneration agent(s) as well as kits comprising the same.

BRIEF DESCRIPTION OF THE DRAWINGS

The file of this patent contains at least one photograph or drawings. For a fuller understanding of the nature and advantages of the present invention, reference should be made to the following detailed description taken in connection with the accompanying drawings, in which:

FIG. 1 depicts the current guidelines for combination therapy for type 1 diabetes as established by Type 1 Diabetes Combination Therapy Assessment Group, Juvenile Diabetes Research Foundation International and Immune Tolerance Network, which not include combination of an immune tolerance agent with an beta regeneration agent or PPI.

FIG. 2 demonstrates human ductal tissue in culture on the left with the transformation into new islets containing glucagon, insulin and somatostatin shown in the right panel in the presence of a regeneration agent.

DEFINITIONS

Figure 3:
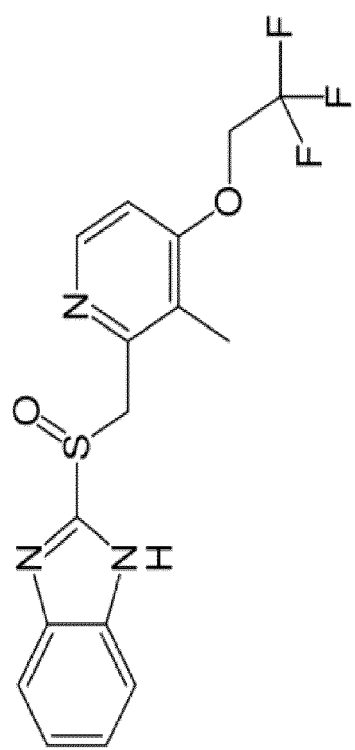
FIG. 3 depicts the structure of the exemplary PPI, Lansoprazole.

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of diabetes, diminishment of extent of disease, delay, slowing, or prevention of disease progression, amelioration, palliation or stabilization of the disease state, and other beneficial results described below. Symptoms of diabetes include low or inadequate levels of insulin or insulin activity, frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections, hyperglycemia, loss of glycemic control, fluctuations in postprandial blood glucose, fluctuations in blood glucagon, fluctuations in blood triglycerides. Diabetes may be diagnosed by methods well known to one of ordinary skill in the art. For example, commonly, diabetics have a plasma blood glucose result of greater than 126 mg/dL of glucose. Pre-diabetes, which may also be treated by the compositions and methods of the invention is commonly diagnosed in patients with a blood glucose result between 100 and 125 mg/dL of glucose. Other symptoms may also be used to diagnose diabetes, related diseases and conditions, and diseases and conditions affected by diminished pancreatic function.

As used herein, "reduction" of a symptom or symptoms (and grammatical equivalents of this phrase) means decreasing of the severity or frequency of the symptom(s), or elimination of the symptom(s).

As used herein, "impaired glucose homeostasis" is a diminished capacity in a subject for regulating glucose by a system of feedback controls, so as to stabilize health and functioning. Conditions that are associated with or are a risk factor for impaired glucose homeostasis include new onset type 1 and 2 diabetes, previously existing type 1 and 2 diabetes, latent autoimmune diabetes of adulthood (LADA), glutamic acid decarboxylase-65 autoimmunity, prediabetes, metabolic syndrome. hyperglycemia, glucose intolerance, beta cell impairment or deficiency, insulin resistance, obesity, polycystic ovarian syndrome, nonalcoholic steatohepatitis, hyperlipidemia, and hypertriglyceridemia.

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "subject" or "patient" is a mammal, typically a human, but optionally a mammalian animal of veterinary importance, including but not limited to horses, cattle, sheep, dogs, and cats. "Patient" and "subject" may be used interchangeably herein.

As used herein, a "therapeutically effective amount" of a drug or agent is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "therapeutically effective amount" of a drug may also be an amount of a drug that when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a therapeutically effective amount may be administered in one or more administrations.

As used herein, an "effective amount" of a drug or agent (and grammatical equivalents of this phrase, e.g. "amount of X that is effective") is an amount of a drug or agent that will have the intended pharmacological or pharmacodynamic effect. The "effective amount" may apply to in vivo, in vitro, or ex vivo applications of the drug or agent.

As used herein in vitro is in cell culture, ex vivo is a cell that has been removed from the body of a subject and in vivo is within the body of a subject.

Abbreviations used herein include PPI for proton pump inhibitor and NOD for non-obese diabetic.

DETAILED DESCRIPTION OF THE INVENTION

The present invention relates to novel therapies, pharmaceutical compositions and methods for insulin independence utilizing PPIs and immune tolerance agents in combination, which have never previously been used together for the treatment of type 1 diabetes.

Methods, pharmaceutical compositions and therapies novel to the prior art are utilized to render patients with recent onset and existing type 1 diabetes, insulin independent by utilizing PPIs and an immune tolerance agent. Not wishing to be bound by theory, PPIs may increase beta cell generation by their properties of increasing plasma gastrin levels, which in turn transforms extra-islet pancreatic ductal tissue into new beta cells. PPIs have never been utilized with an immune tolerance agent, which this invention demonstrates is required to protect new beta cells formed by the PPI from autoimmune destruction.

This invention also provides for novel therapies, pharmaceutical compositions and methods for insulin independence among type 2 diabetes patients using PPIs alone or in combination with other therapies. Although gastrin has been used alone and in combination with other growth factors in clinical trials among patients with type 1 diabetes, the combination of gastrin or usage of a PPI with an immune tolerance agent has never previously been proposed or utilized in clinical trials for type 1 diabetes patients.

This invention describes therapeutics and pharmaceutical compositions and therapeutic combinations that have not been described in the prior art for insulin-independence among type 1 and type 2 diabetes, utilizing PPIs as a novel usage for stimulating the formation of new beta cells for patients with type 1 and 2 diabetes. The usage of gastrin and other beta regeneration agents has shown the ability to reverse type 1 mouse models (NOD) alone without an immune tolerance agent to protect new beta cells formed from gastrin. Suarez-Pinzon W L et al. Diabetes. 2005; 54(9):2596-601. This inventor does not find that gastrin alone or even a combination of beta cell growth factors are enough to sustain insulin independence in men.

Complex differences exist between mice and men, including the much faster beta cell turnover rates among beta cells in mice compared to men. In man, there is a different composition of the islets along with different cell types within the islet of man compared to mice and that 70% or more of beta cells are communicating with other islet cell types that are not contained within the mouse islets. Levetan C. J. Diabetes. 2010; 2(2):76-84 This invention provides a new model for treatment of type 1 and 2 diabetes, and based upon the complexity and distinctions between the islets of mice and men, this invention provides for novel therapies, pharmaceutical compositions and methods for insulin independence and provides a methodology for treating patients requiring insulin that have not previously been described.

FIG. 1 shows the prior art therapy considered as "combination therapy" by the Type 1 Diabetes Combination Therapy Assessment Group, Juvenile Diabetes Research Foundation and the International, Immune Tolerance Network, which do not include the combination of an immune tolerance agent with a beta regeneration agent or a proton pump inhibitor. FIG. 1 lists two columns of immune tolerance agents to be placed in combination with one another with no mention whatsoever for the need of a beta regeneration agent, or any other agents for the treatment of type 1 diabetes other than immune modulation agents.

This invention redefines combination therapy in type 1 diabetes, which has been considered a combination of more than one immune tolerance agents, whereas this invention defines combination therapy as being an immune tolerance agent and a regeneration agent. This invention finds that among patients with type 1 diabetes, endogenous insulin production generated by PPIs must be used in combination with an immune tolerance agent to protect the new beta cells formed from PPIs and together there is the ability to generate new and protected beta cells that render patients insulin-free. This invention provides new and unique methods, therapeutics and pharmaceutical compositions for insulin-independence among patients with type 1 diabetes. This invention provides new art providing for the usage of PPIs, when added to diabetes therapeutics, to allow for insulin-independence among patients with type 2 diabetes.

Reference will now be made in detail to various exemplary embodiments of the invention. The following detailed description is presented for the purpose of describing certain embodiments in detail. The present invention may be further illustrated in the following figures, attention being called to the fact, however, that the embodiments described in the description and shown in the figures are illustrative only and are not intended to limit the scope of the invention, and that changes may be made in the specific constructions described in this specification and accompanying drawings that a person of ordinary skill in the art will recognize are within the scope and spirit of the invention. The true scope of the invention is defined by the claims. Further, any features of any embodiment described herein are equally applicable to any other embodiment described herein or envisioned by one of ordinary skill in the art. The detailed description and figures provided herein should not be construed to exclude features otherwise described with respect to another embodiment.

In one embodiment, the present invention provides a method of treating recent onset, existing type 1 diabetes and Latent Autoimmune Diabetes of Adulthood (LADA) by administration of a PPI in combination with an immune tolerance agent to a patient in need thereof. Not wishing to be bound by theory, the use of a PPI may generate an increase in plasma gastrin that transforms pancreatic extra-islet ductal tissue into new beta cells and confers specific regenerative capacity on the human pancreas, while the use of an immune tolerance agent may protect the newly formed beta cells from destruction. The combination of a PPI and an immune tolerance agent may reduce or eliminate the need for exogenous insulin dependence in these patients.

The PPI may also be used in combination with other beta regeneration agents including, but not limited to Reg Peptides, Optimized Reg Peptide formulations and/or agents that bind to the human Reg Receptor. A combination of the PPI alone or with other beta regeneration agents AND one or more immune tolerance agent(s) is used in this invention to generate new beta cells and protect newly formed beta cells from autoimmune destruction.

Exemplary PPIs that may be used in the invention include, but are not limited to Omeprazole (brand names: GASEC, LOSEC, PRILOSEC, ZEGERID, OLID, LOMAC, OMEPRAL, OMEZ) Lansoprazole (brand names: PREVACID, ZOTON, MONOLITUM, INHIBITOL, LEVANT, LUPIZOLE), Dexlansoprazole (brand name: KAPIDEX, DEXILANT), Esomeprazole (brand names: NEXIUM, ESOTREX, ESSO), Pantoprazole (brand names: PROTONIX, SOMAC, PANTOLOC, PANTOZOL, ZURCAL, ZENTRO, PAN, CONTROLOC), Rabeprazole (brand names: ACIPHEX, PARIET, ERRAZ, ZECHIN, RABECID, NZOLE-D, RABELOC, RAZO. DORAFEM) and Ilaprazole.

FIG. 2 shows the ability of human ductal tissue to be transformed into insulin-secreting islets in presence of gastrin and other regenerating agents.

FIG. 3 shows the structure of the exemplary PPI, Lansoprazole (1H-Benzimidazole,2-[[[3-methyl-4-(2,2,2-trifluoroethoxy)-2-pyridinyl]methyl]sulfinyl]-2-[[[3-Methyl-4-(2,2,2-trifluoroethoxy)-2-pyridyl]-methyl]sulfinyl] benzimidazole).

Exemplary immune tolerance agent(s) that may be used include, but are not limited to: Cyclosporine, Anti CD-3 antibodies including hOKT3γ1(Ala-Ala) and ChAglyCD3 that target the immune response and specifically block the T-lymphocytes that cause beta cell death in type 1 diabetes; Sirolimus (Rapamycin); Tacrolimus (FK506); Etanercept, Alefacept, Belatacept, a heat-shock protein 60 (Diapep277); a tuberculosis vaccine, Glutamic Acid Decarboxylase 65 (GAD65) vaccine; the BCG tuberculosis vaccine also known as Bacillus Calmette-Guérin or Bacille Calmette-Guérin/BCG Vaccine, Mycophenolate Mofetil alone or in combination with Daclizumab; the anti-CD20 agent, Rituximab; Campath-1H (Anti-CD52 Antibody), lysofylline; antithymocyte globulin (ATG), Proleukin and those the combination of Proleukin and Rapamune, Vitamin D (Vitamin D2, D3, 1.25 dihydroxy D and other Vitamin D preparations), IBC-VSO vaccine, Ex vivo Expanded Human Autologous CD4+ CD127lo/−CD25+ Polyclonal Regulatory T Cells; interferon-alpha; a vaccine using $CD4^+CD25^+$ antigen-specific regulatory T cells, Interleukin-1 Receptor Antagonist (anakinra), and Alpha 1-Antitrypsin.

Figure 4:
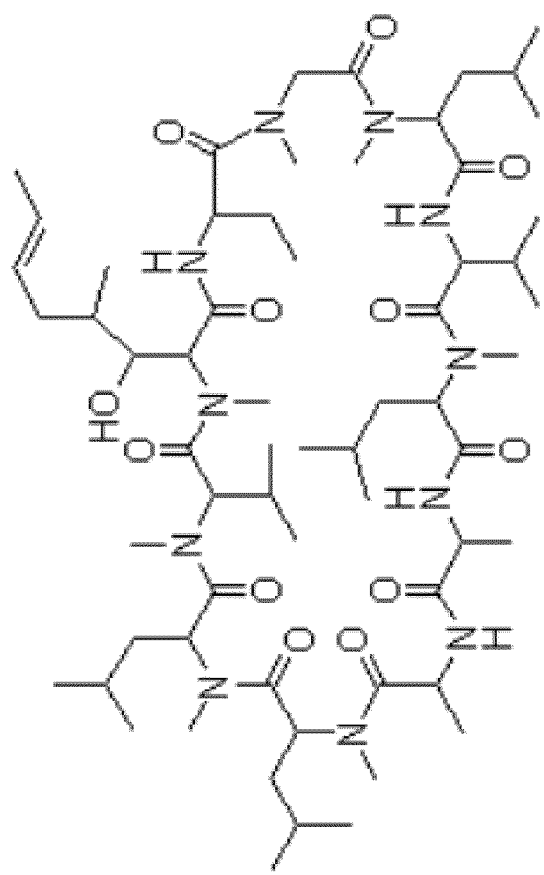
FIG. 4 depicts the structure of the exemplary immune tolerance agent, Cyclosporine.

FIG. 4 shows the structure of the exemplary immune tolerance agent, Cyclosporine ((E)-14,17,26,32-tetrabutyl-5-ethyl-8-(1-hydroxy-2-methylhex-4-enyl)-1,3,9,12,15,18,20,23,27-nonamethyl-11,29-dipropyl-1,3,6,9,12,15,18,21,24,27,30-undecaazacyclodotriacontan-2,4,7,10,13,16,19,22,25,28,31-undecaone).

Figure 5:
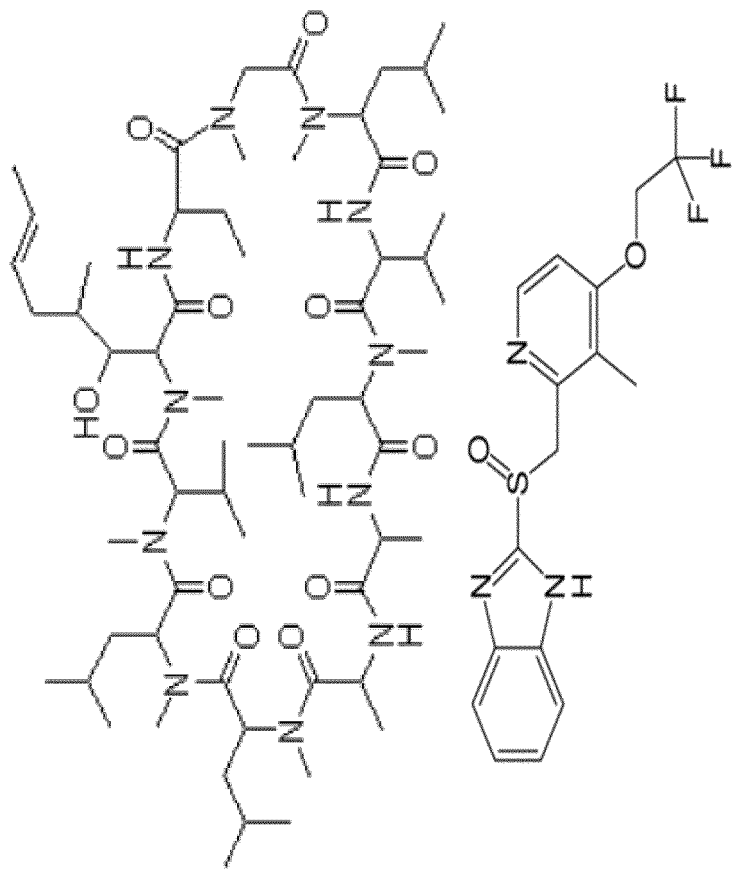
FIG. 5 depicts the structure of the exemplary immune tolerance agent, Cyclosporine formulated in one capsule and oral suspension with exemplary PPI, Lansoprazole enabling protect new beta cells that are formed by the PPI from autoimmune attack. The physical and chemical properties of these two drugs are compatible for co-formulation in pill/capsule and oral suspension form.

FIG. 5 demonstrates the structures of an immune tolerance agent, Cyclosporine, formulated in combination with the PPI, Lansoprazole, to protect new beta cells that are formed by a PPI from autoimmune attack. The physical and chemical properties of these two drugs are compatible for co-formulation in pill/capsule and oral suspension form.

Figure 6:
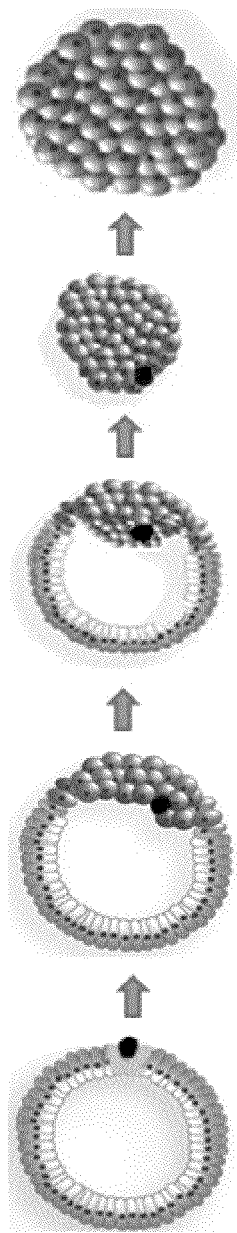
FIG. 6 demonstrates the plasticity of the human ductal tissue and role of PIT induced gastrin illustrated by the black circle binding to a progenitor cell found within the pancreatic extra-islet ductal tissue. The interaction of gastrin indicated by the black circle, with the progenitor begins a transformation process of exocrine tissue transformation into endocrine tissue transformation with the new pancreatic beta cells shown inside the new islet with surrounding alpha cells.

FIG. 6 demonstrates the role of PPI-induced gastrin illustrated by the black circle binding to a progenitor cell found within the pancreatic extra-islet ductal tissue. The interaction of gastrin with the progenitor begins a transformation process of exocrine tissue transformation into endocrine tissue transformation with the new pancreatic beta cells shown inside the new islet with surrounding alpha cells.

This invention identifies that the class of drugs known as PPIs can also be used in the treatment of diabetes, and specifically among patients requiring insulin. Among those patients with autoimmune type 1 diabetes, an immune tolerance agent may be required for effectiveness with a PPI in order to protect new beta cells formed from the PPI from autoimmune destruction. The methods of utilizing a PPI with an immune tolerance agent may render patients with diabetes with more permanent independence than that seen with either an immune tolerance agent alone or gastrin alone. The PPI may also be used in combination with other beta regeneration agents such as a Reg peptide or Reg peptide derivative or Reg peptidomimetic acting on the Reg receptor.

Figure 7:
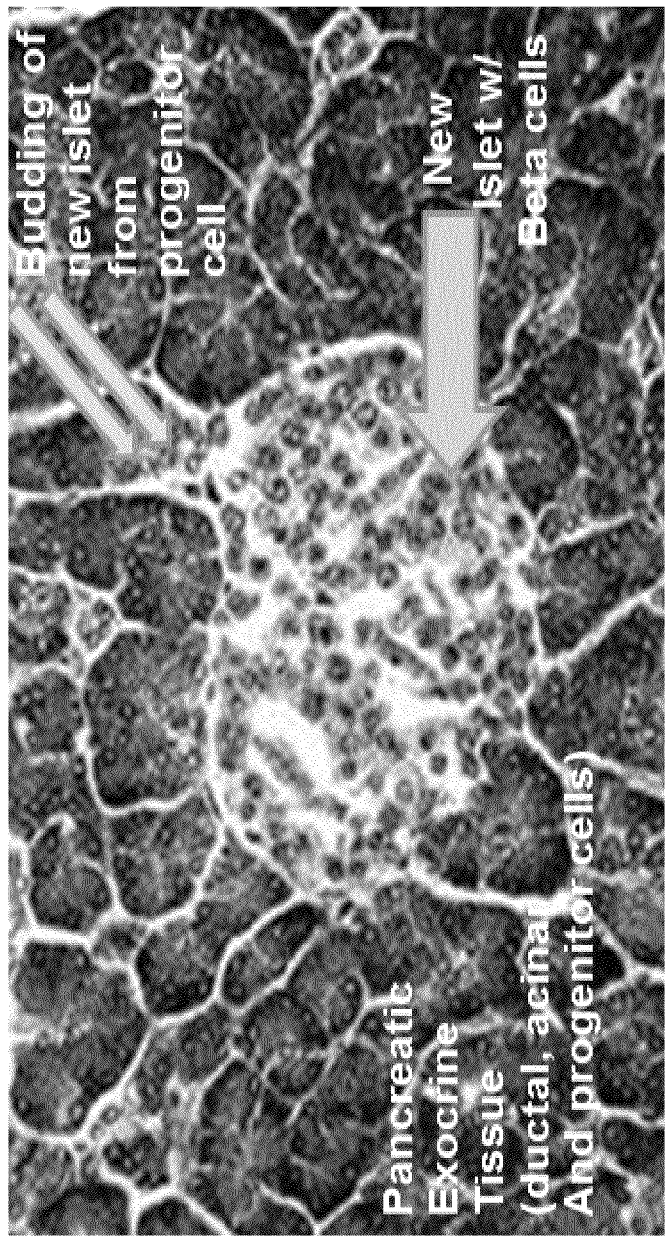
FIG. 7 demonstrates an actual islet containing islet structure that has been generated from the surrounding extra-islet ductal tissue in the presence of gastrin.

FIG. 7 demonstrates an actual islet containing islet structure that as been generated from the surrounding extra-islet ductal tissue in the presence of gastrin.

In another embodiment, methods for treating a pathology associated specifically with impaired pancreatic function in a subject is provided. The method comprises the steps of administering a PPI with an immune tolerance agent. The method may further comprise one or more of the steps of (1) intensifying glycemic control (2) administering oral vitamin D to maintain 25-hydroxyvitamin levels above 40 mg/ml; (3) reducing, or tapering off of other diabetes therapies as new beta cell populations are restored (4) lowering the dosage of the immune tolerance agent and the PPI as dosages of other diabetes medication, including insulin, are tapered off and (5) administering the lowest dosage formulations of PPIs alone and in combination with immune tolerance agents at intervals to maintain a minimum number of beta cells for normal glucose metabolism.

Figure 8:
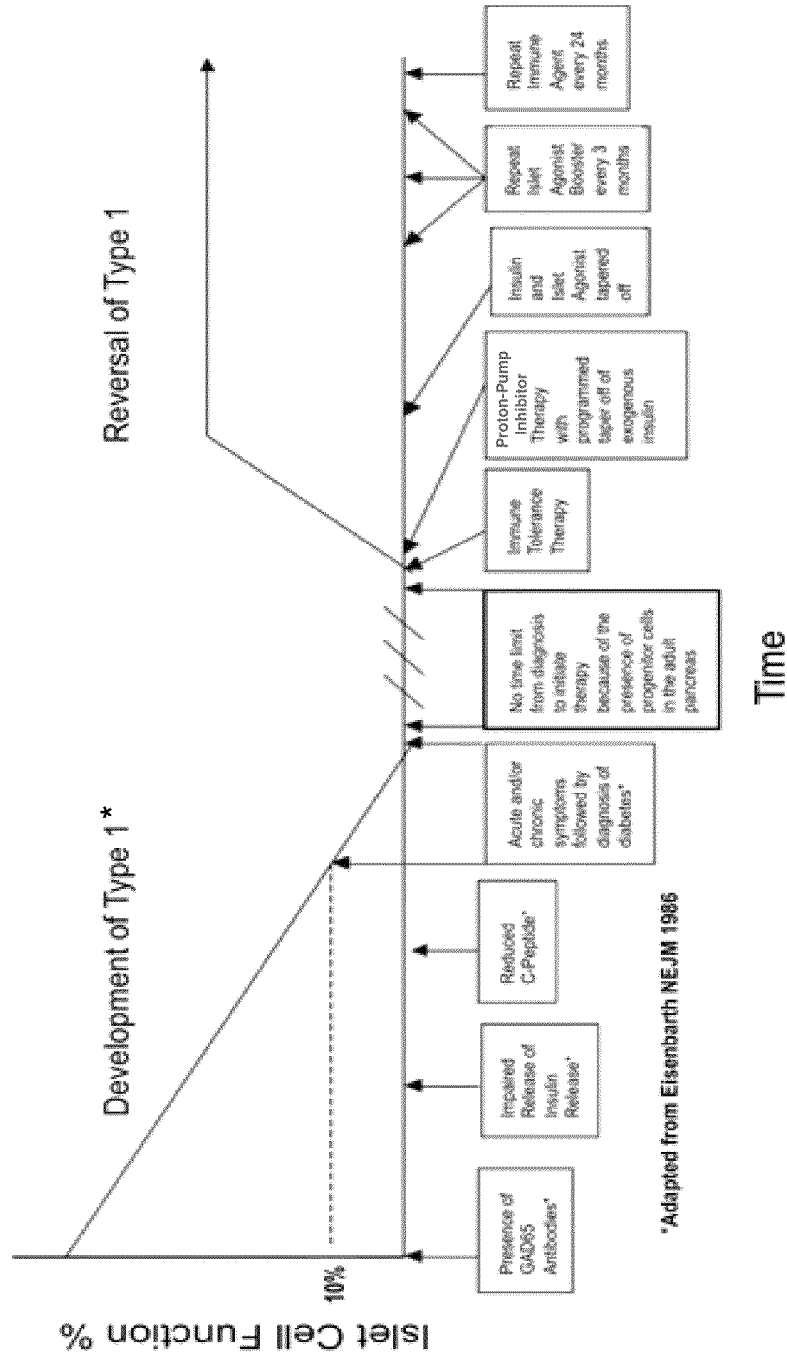
FIG. 8 demonstrates the methods for treating a patient with type 1 diabetes with an immune tolerance agent and a PPI for insulin independence.
Figure 9:
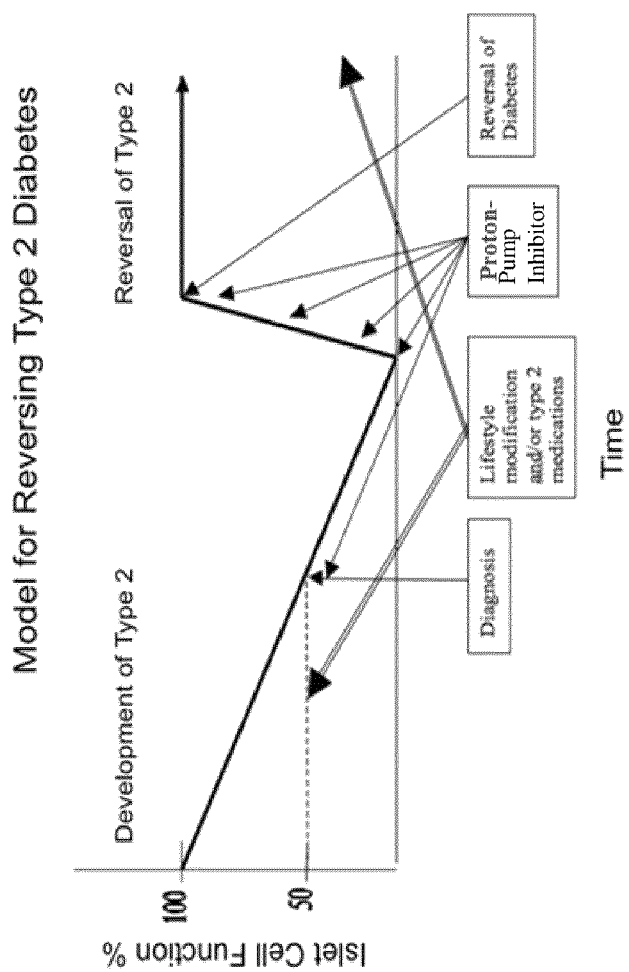
FIG. 9 is an illustration of the methodology to reverse new onset or existing type 2 diabetes utilizing a PPI for insulin independence.
Figure 10:
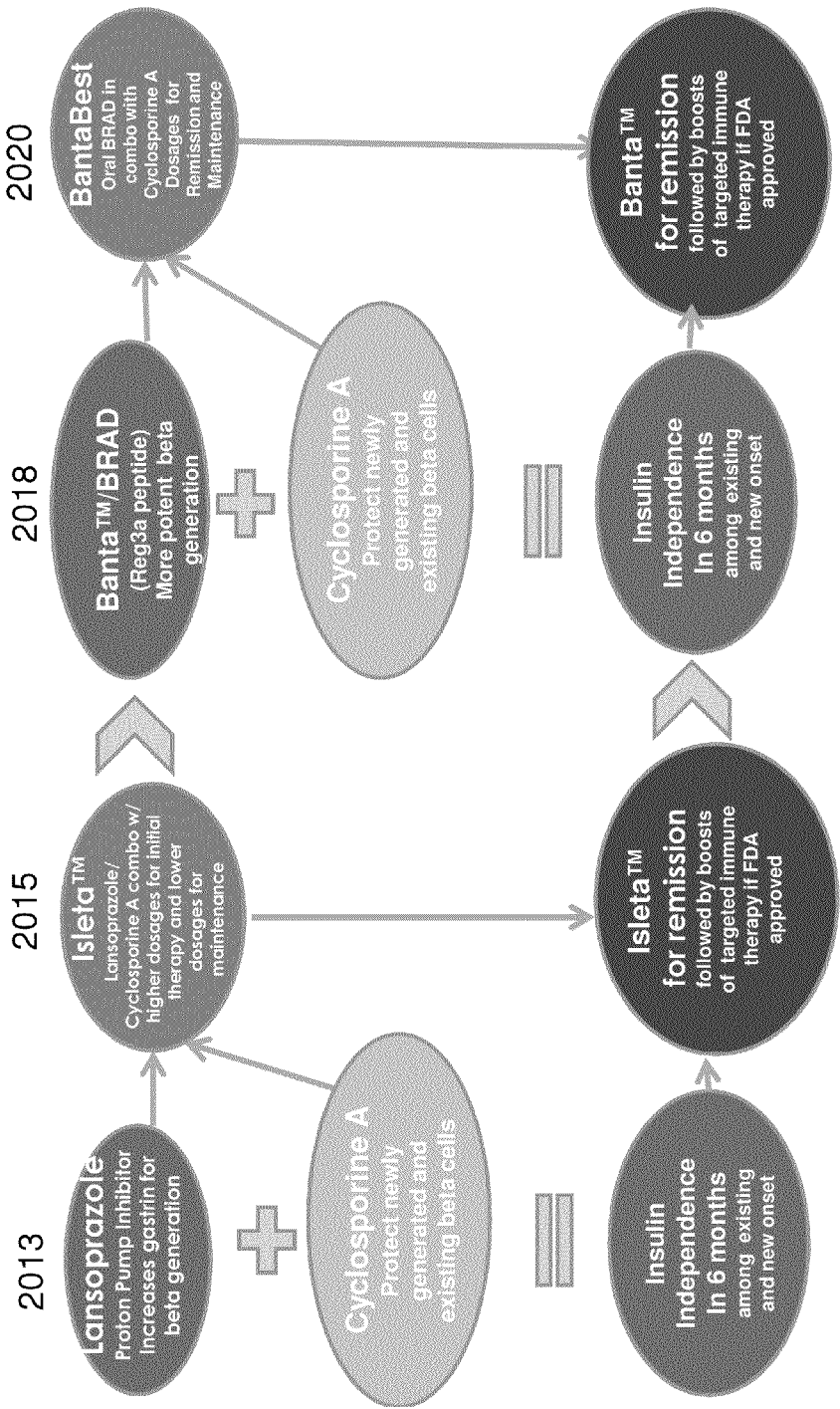
FIG. 10 is an illustration of the potential of the currently PPI and immune tolerance agents in combination with one another as a platform for the development of many future therapies for insulin independence among type 1 patients as better and more potent beta regeneration and immune tolerance become available.

FIG. 8 demonstrates exemplary methods for using a PPI in combination with an immune tolerance agent among patients with type 1 diabetes on insulin. The PPIs may be used alone or in combination with another beta regeneration agent, such as a Reg peptide or Reg peptide derivative or Reg peptidomimetic acting on the Reg receptor and then added to the patient's current diabetes drug regiment, with the ability to taper insulin as a result of new insulin-producing beta cells being generated. FIG. 9 demonstrates an exemplary method for treating patients with type 2 diabetes using a PPI. FIG. 10 is an illustration of the potential of the currently PPI and immune tolerance agents in combination with one another as a platform for the development of many future therapies for insulin independence among type 1 patients as better and more potent beta regeneration and immune tolerance become available.

During the process of new beta cell formation from extra-islet ductal tissue, it is critical that glucose levels remain within a narrow range. Because of the many redundant mechanisms in the body to prevent hypoglycemia including the secretion of epinephrine, norepinephrine, cortisol and growth hormone to protect against hypoglycemia, hypoglycemia is a contraindication for growth of new beta cells. Similarly if glucose levels are markedly elevated, there is glucose toxicity to beta cells, thus beta regeneration in the presence of a beta promoting agent like gastrin is best given with a meal when there will be a peak post-meal glucose level. Thus, the PPI, for beta regeneration is dosed with breakfast and dinner. Significant hypoglycemia in patients, would not be optimal for beta regeneration outcomes from gastrin. Compared to rodents, glucose levels are slightly lower in humans. Despite this difference, homeostasis is maintained within a very narrow range in both species, due to the exquisite intercommunication within the islet complex. Sensor data from non-diabetic humans demonstrate that 80% of all measured glucose levels lie within 60-100 mg/dL, with mean peak glucose levels after meals of <120 mg/dL. Linear regression curves from the Diabetes Control and Complications Trial (DCCT) and the United Kingdom Prospective Diabetes Study (UKPDS) show that A1C levels above 5.5% are associated with more complications. This data is supported by A1C levels from the EPIC-Norfolk trial among non-diabetic individuals, which found that A1C levels above 5.5% are associated with significantly increased risks for vascular-related morbidity and mortality.

Glucose homeostasis requires an adequate number of completely functional islets, as illustrated by the inability to restore normoglycemia among diabetic patients even when intensive regimens of insulins are utilized. The DCCT investigators set, as a major treatment outcome goal, a mean A1C over the trial period of ≤6.05% without an increased risk for hypoglycemia This goal was not achieved with only replacing insulin, that is, only one of the multiple hormones missing in diabetes. The relationship between distinct cell types within the islet and the accompanied islet abnormalities in resulting from beta cell loss, including dysfunction with amylin, glucagon, somatostatin, pancreatic polypeptide and islet ghrelin had yet to be and continues to be elucidated.

Sensor-augmented pumps recently were shown to improve A1C levels from 8.3% to 7.5% over 12 months, with further reductions to 7.4% after an additional 6 months of treatment. These achievements were made without the associated weight gain or hypoglycemia seen in the DCCT. Despite technological advances in sensors and pumps, sensor-augmented pump therapy did not improve A1C levels as much as those seen in the DCCT decades ago. This underscores the importance of restoring beta function and communication within the islet complex.

For example, a clinical study by this inventor, has been designed to use these two FDA approved drugs (one a PPI and one an immune tolerance agent) in a 4-arm clinical trial to determine the efficacy of the combination of the PPI alone with a placebo compared to an immune tolerance agent alone compared to both agents and an arm with only placebo agents. These studies separately evaluate those with recent onset (less than 12 from diagnosis) and The glucose goals would be 100 mg/dL range before meals and 140 mg/dL two hours after meals. Once patients are enrolled in such a trial, patients glucose levels will be monitored carefully with basal insulin levels reduced by 10% when fasting glucose levels fall below 80 mg/dL. If premeal glucose levels are trending downward from baseline a 10% reduction in both the meal in which the premeal glucose level is below 100 and the meal prior to that meal. Any symptomatic lows must be immediately reported with the Physician Investigator, to appropriately reduce either the basal or bolus insulin with the goal of glucose levels in the 100 mg/dL range before meals and 140 mg/dL range 2 hours after meals.

For patients on insulin with type 2, based upon glucose levels, other diabetes medications, including insulin could be tapered if premeal glucose levels are less than 100 mg/dL and hypoglycemia episodes occur. If the fasting glucose if less than 80 mg/dL, the basal insulin will be decreased by 10% and if the premeal glucose level is <80 mg/dL, there would be a 10% lowering of insulin at both the present meal and the prior meal.

Many patients with type 2 diabetes and PreDiabetes may be on one or more agents, which may include a combination of agents which may improve existing beta cell function and glucose metabolism. Patients with type 2 diabetes may already be on other diabetes agents including: all types of insulin, Glucagon Like Peptide-1 (GLP-1) receptor analogs Liraglutide and Exenatide, Dipeptidyl Peptidase-4 Inhibitors, (DPP-4 inhibitors), and including (Sitagliptin, Saxagliptin, Linagliptin), the Amylin analog, pramlintide, acarbose, orlistat, colesevelam, bromocriptine, orlistat, combination therapies with the biguanide, metformin, and combinations of with thiazolidinediones, sulfonylureas and DPP-4 inhibitors and new agents SGLT2 inhibitors (dapagliflozin and canagliflozin). The goal in adding a PPI is the ability to taper insulin due to the generation of new beta cells. The ability to provide patients with type 2 diabetes with new beta cells may enable tapering of their insulin and other agents and may potentially be tapered later if glucose levels and hemoglobin A1C fall into the normal range.

In another embodiment, the present invention provides for methods of treating new and existing type 1 and 2 diabetes, PreDiabetes or diseases of insulin deficiency, beta cell deficiency, insulin resistance and impaired glucose metabolism by use of a PPI alone or in combination with another beta regeneration agent or agent for the ex vivo transformation of new beta cells from extra-islet ductal cells. The other beta regeneration agent(s) may include but is not limited to Reg Peptides, Optimized Reg Peptide formulations and/or agents that bind to the human Reg Receptor.

The extra-islet ductal cells may be obtained from a subject by any technique known in the art, including, but not limited to, biopsies, scrapings, and surgical tissue removal. The isolated extra-islet ductal cells may be transformed into beta cells by contacting them in culture with a PPI alone or combination with other beta regeneration agents for a sufficient amount of time, e.g., 2, 4, 6, 8, 10, 12, 18, 24, 36, 48, hours or more, and in a sufficient amount to allow transformation into beta cells. Methods for culturing primary cells for short periods of time are well known in the art. For example, cells may be cultured in plates (e.g., in microwell plates) either attached or in suspension.

Figure 11:
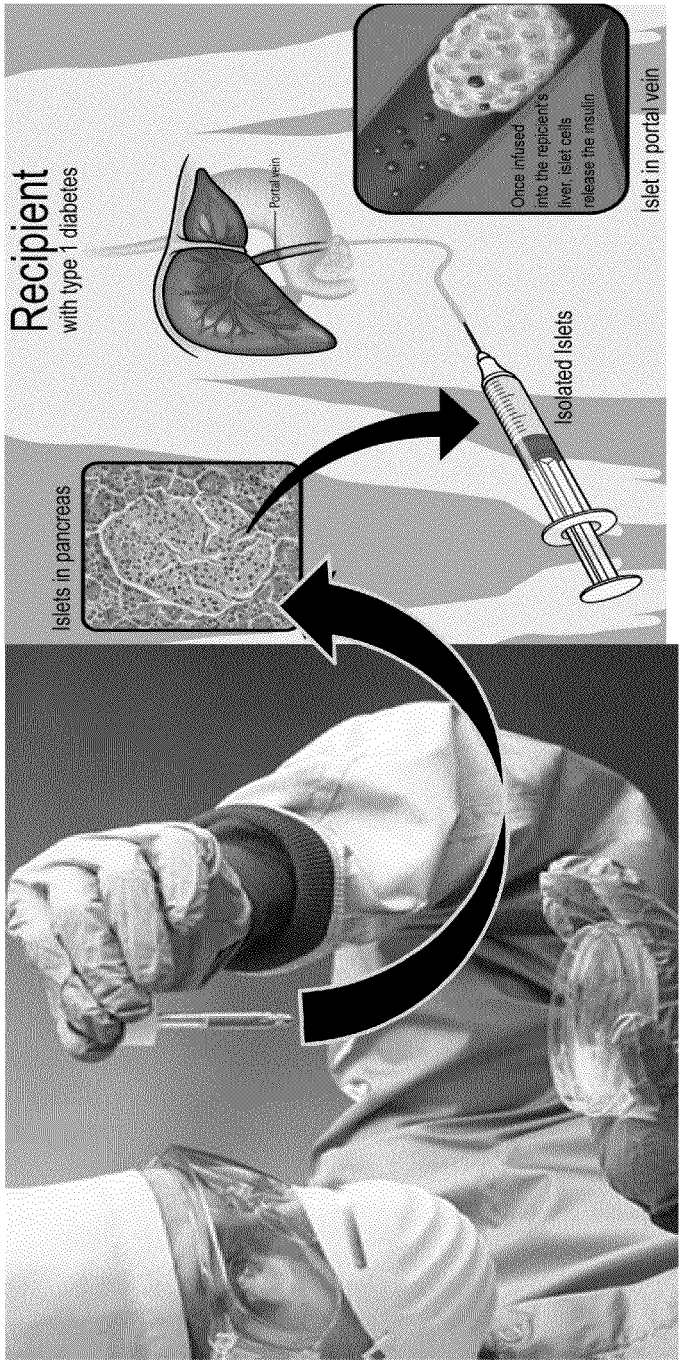
FIG. 11 is an illustration of the methodology for delivering newly formed beta cells to patients that are generated ex vivo by using a PPI used alone or in combination with other beta regeneration agents, which may include but are not limited to Reg Peptides, Optimized Reg Peptide formulations and/or agents that bind to the human Reg Receptor for the ex vivo transformation of new beta cells from pluripotent stem cells.

In another embodiment, the invention provides methods of using a PPI for the ex vivo transformation of new beta cells from pluripotent stem cells. Methods for the formation and delivery of new beta cells generated ex vivo by utilizing gastrin to stimulate new beta cells from pluripotent stem cells are shown in FIG. 11. The pluripotent stem cells may include embryonic cells, adult somatic stem cells, human adult bone-marrow derived stem cells, umbilical cord stems cells, mesenchymal stem cells, human amniotic membrane-derived mesenchymal cells, mammalian stem cells, ectodermal stem cells or other stem cells and may include resident populations of endogenous stem cells that exist within the adult pancreas. The PPI may be used alone or in combination with other beta regeneration agents, which may include but are not limited to Reg Peptides, Optimized Reg Peptide formulations and/or agents that bind to the human Reg Receptor.

The pluripotent cells may be obtained from a subject by any technique known in the art. The isolated pluripotent cells may be transformed into beta cells by contacting them in culture with a PPI alone or combination with another beta regeneration agent for a sufficient amount of time, e.g., 2, 4, 6, 8, 10, 12, 18, 24, 36, 48, hours or more, and in a sufficient amount to allow transformation into beta cells. Methods for culturing pluripotent cells for short periods of time are well known in the art.

Transformation of extra-islet ductal tissue or pluripotent cells into beta cells may be confirmed by measuring insulin secretion into the culture media. At some point after transformation of the extra-islet ductal tissue or pluripotent cells into new beta cells, the new beta cells are introduced into the subject. The new beta cells are administered to patients with new and existing type 1 and 2 diabetes, PreDiabetes or diseases of insulin deficiency, beta cell deficiency, insulin resistance and impaired glucose metabolism, with routes of delivery to include, but are not limited to the portal and umbilical vein, oral, intravenous, subcutaneous delivery with and without organ specific targeting and may include direct administration to the pancreas or liver.

In another embodiment, this invention provides a method for treating new onset or existing type 1 diabetes and LADA through ex vivo administration of new beta cells formed by contacting extra-ductal cells or pluripotent stem cells in culture with a PPI used alone or in combination with another beta regeneration agent or agents. The new beta cells are administered to a patient in combination with one or more immune tolerance agents to protect the new beta cells delivered to the patient with diabetes from autoimmune destruction. The other beta regeneration agent(s) may include, but is not limited to Reg Peptides, Optimized Reg Peptide formulations and/or agents that bind to the human Reg Receptor. The immune tolerance agents may include, but are not limited to Cyclosporine, Anti CD-3 antibodies including hOKT3γ1 (Ala-Ala) and ChAglyCD3 that target the immune response and specifically block the T-lymphocytes that cause beta cell death in type 1 diabetes; Sirolimus (Rapamycin); Tacrolimus (FK506); Etanercept, Alefacept, Belatacept, a heat-shock protein 60 (Diapep277); a tuberculosis vaccine, Glutamic Acid Decarboxylase 65 (GAD65) vaccine; the BCG tuberculosis vaccine also known as Bacillus Calmette-Guérin or Bacille Calmette-Guérin/BCG Vaccine, Mycophenolate Mofetil alone or in combination with Daclizumab; the anti-CD20 agent, Rituximab; Campath-1H (Anti-CD52 Antibody), lysofylline; antithymocyte globulin (ATG), Proleukin and those the combination of Proleukin and Rapamune, Vitamin D (Vitamin D2, D3, 1.25 dihydroxy D and other Vitamin D preparations), IBC-VSO vaccine, Ex vivo Expanded Human Autologous CD4+CD127lo/−CD25+ Polyclonal Regulatory T Cells; interferon-alpha; a vaccine using CD4$^+$ CD25$^+$ antigen-specific regulatory T cells, Interleukin-1 Receptor Antagonist (anakinra), and Alpha 1-Antitrypsin.

In one embodiment, the immune tolerance agent is administered to patients with type 1 diabetes or LADA simultaneously with the administration of new beta cells generated by ex vivo production to protect the new beta cells from autoimmune destruction. In another embodiment, an immune tolerance agent is administered to patients with type 1 diabetes or LADA beginning prior to the time that they are administered the new beta cells generated by ex vivo production to protect the new beta cells from autoimmune destruction.

In another embodiment, the invention provides a method for treating PreDiabetes, new onset or pre-existing type 2 diabetes comprising administration of a PPI to a patient alone or in combination with another beta regeneration agent or agents to accelerate the formation of new pancreatic beta cells generated ex vivo that are administered to patients who are diabetes-drug naïve. The other beta regeneration agent(s) may include, but is not limited to Reg Peptide(s) and includes formulations, derivatives, optimized forms and peptidomimetics of Reg Peptides.

This invention also includes methods for pancreatic beta cell generation and include both in vivo and ex vivo beta cell generation and methods for treating a condition that is associated with or is a risk factor for impaired glucose homeostasis. The condition that is associated with or is a risk factor for impaired glucose homeostasis may include, but is not limited to new onset and previously existing type 1 and 2 diabetes, Latent Autoimmune Diabetes of Adulthood (LADA), those at risk for type 1 diabetes, including but not limited to those with positive autoimmune antibodies markers including who are Glutamic Acid Decarboxylase-65 antibody, those with Pre-Diabetes or diseases of hyperglycemia, glucose intolerance and beta cell impairment or deficiency, insulin resistance, associated conditions including, obesity, obesity prior to the development of diabetes, obesity in children leading to PreDiabetes, both type 1 and type 2 diabetes in childhood and adolescence and include, but are not limited to conditions such as polycystic ovarian syndrome, nonalcoholic steatohepatitis, hyperlipidemia and hypertriglyceridemia and other conditions related to the deficiency or lack of effective amounts of insulin.

In one embodiment, patients with a condition that is associated with or is a risk factor for impaired glucose homeostasis are administered beta cells generated from ex vivo production induced by a PPI alone or in combination with another beta regeneration agent or agents. The beta cells may be generated from extra-islet ductal tissue or pluripotent cells contacted in an ex vivo culture with a sufficient amount of a PPI alone or in combination with another beta regeneration agent(s) using cell culture techniques known in the art. The other beta regeneration agent(s) may include, but is not limited to Reg Peptide(s) and includes formulations, derivatives, optimized forms and peptidomimetics of Reg Peptides. In another embodiment, patients receiving beta cells generated from ex vivo production induced by PPIs alone or in combination with another beta regeneration agent(s) are also administered an immune tolerance agent to protect new ex vivo-generated beta cells from immune attack. The immune tolerance agent may be administered to the patient before and/or in parallel with the administration of the new beta cells.

In another embodiment, the invention provides a method of treating a condition that is associated with or is a risk factor for impaired glucose homeostasis comprising administration of a PPI to a patient to generate new beta cells in vivo. The condition of impaired glucose homeostasis may include, but is not limited to new onset and previously existing type 2 diabetes, PreDiabetes, glucose intolerance, hyperglycemia, syndromes of insulin resistance and glucose impairment, diseases of hyperglycemia, glucose intolerance and beta cell impairment or deficiency, insulin resistance and associated conditions including: obesity, obesity prior to the development of diabetes, obesity in children leading to PreDiabetes, childhood diabetes (both type 1 and 2) and other conditions including but not limited to polycystic ovarian syndrome, nonalcoholic steatohepatitis, hyperlipidemia and hypertriglyceridemia and other conditions related to the deficiency or lack of effective amounts of insulin. The PPI is administered to the subject in an amount that is effective for generating new beta cells in the pancreas of the subject and/or reducing or preventing symptoms of the condition. The PPI may be administered alone or in combination with another beta regeneration agent or agents which may include, but is not limited to Reg Peptide(s), including formulations, derivatives, optimized forms and peptidomimetics of the Reg Peptides. The other beta regeneration agent(s) is administered to the subject in an amount that is effective for generating new beta cells in the pancreas of the subject and/or reducing or preventing symptoms of the condition. The patient may be diabetes drug naïve or on one or more diabetes agents, which may include all types of insulin, sulfonylureas, metformin, meglitinides, GLP-1 receptor analogs, DPP-4 inhibitors, thiazolidinediones, SGLT2 inhibitors, anti-inflammatory agents, pramlintide, Vitamin D and/or lifestyle modifications and other agents utilized to improve glucose in order to prevent and limit the destruction of the new beta cells formed by this invention. In one embodiment, the PPI is administered with an immune tolerance agent. The immune tolerance agent is administered to the patient in an amount that is effective for protecting the new beta cells from destruction from the immune system and/or reducing or preventing symptoms of the condition.

For in vivo methods, the PPI(s), other beta regeneration agent(s), and immune tolerance agent(s) described herein may be administered to a patient in pharmaceutically acceptable carriers, such as, for example, solutions, suspensions, tablets, capsules, ointments, elixirs, and injectable compositions. Pharmaceutical compositions may contain from 0.01% to 99% by weight of the PPI(s), other beta regeneration agent(s), and immune tolerance agent(s). Compositions may be either in single or multiple dose forms. The amount of PPI(s), other beta regeneration agent(s), and immune tolerance agent(s) in any particular pharmaceutical composition will depend upon the effective dose, that is, the dose required to regenerate new beta cells and protect them from destruction by the immune system.

Pharmaceutically acceptable carriers include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the PPI(s), other beta regeneration agent(s), and immune tolerance agent(s) are dissolved or suspended in suitable liquids, such as fatty oils, or liquid paraffin, optionally with stabilizers.

Fatty oils may comprise mono-, di- or triglycerides. Mono-, di- and triglycerides include those that are derived from C6, C8, C10, C12, C14, C16, C18, C20 and C22 acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355. Other triglycerides are caprylic-capric acid triglycerides such as known and commercially available under the trade name MYRITOL, including the product MYRITOL 813. Further triglycerides of this class are CAPMUL MCT, CAPTEX 200, CAPTEX 300, CAPTEX 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

Possible pharmaceutical preparations which can be used rectally include, for example, suppositories, which consist of a combination of one or more of the PPI(s), other beta regeneration agent(s), and immune tolerance agent(s) with a suppository base. Suitable suppository bases are, for example, natural or synthetic triglycerides, or paraffin hydrocarbons. In addition, it is also possible to use gelatin rectal capsules which consist of a combination of the PPI(s), other beta regeneration agent(s), and immune tolerance agent(s) with a base. Possible base materials include, for example, liquid triglycerides, polyethylene glycols, or paraffin hydrocarbons.

Suitable formulations for parenteral administration include aqueous solutions of the PPI(s), other beta regeneration agent(s), and immune tolerance agent(s) in water-soluble form, for example, water-soluble salts and alkaline solutions. In addition, suspensions of the PPI, other beta regeneration agent(s), and immune tolerance agent(s) as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions may be formulated as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams may be formulated from a mixture of mineral oil, self-emulsifying beeswax and water in which the PPI(s), other beta regeneration agent(s), and immune tolerance agent(s), dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a suspension of the PPI(s), immune tolerance agent(s), or additional beta regeneration agent(s) in a vegetable oil such as almond oil with warm soft paraffin and allowing the mixture to cool. A typical example of such an ointment is one which includes about 30% almond oil and about 70% white soft paraffin by weight.

Lotions may be conveniently prepared by preparing a suspension of the PPI(s), other beta regeneration agent(s), and immune tolerance agent(s) in a suitable high molecular weight alcohol such as propylene glycol or polyethylene glycol.

Suitable routes of administering the pharmaceutical preparations include oral, rectal, topical (including dermal, buccal and sublingual), vaginal, parenteral (including subcutaneous, intramuscular, intravenous, intradermal, intrathecal, intratumoral, and epidural) and by naso-gastric tube. It will be understood by those skilled in the art that the preferred route of administration will depend upon the condition being treated and may vary with factors such as the condition of the recipient.

The PPI(s), other beta regeneration agent(s), and immune tolerance agent(s) may be administered with other diabetes agents including, but not limited to, all types of insulin, Glucagon Like Peptide-1 (GLP-1) receptor analogs Liraglutide and Exenatide, Dipeptidyl Peptidase-4 Inhibitors, (DPP-4 inhibitors), and including (Sitagliptin, Saxagliptin, Linagliptin), the Amylin, analog, pramlintide, acarbose, orlistat, colesevelam, bromocriptine, orlistat, combination therapies with the biguanide, metformin, and combinations of with thiazolidinediones, sulfonylureas and DPP-4 inhibitors and new agents SGLT2 inhibitors (dapagliflozin and canagliflozin).

This invention also includes a pharmaceutical composition which formulates a PPI with an immune tolerance agent. In one embodiment, the invention provides a combination product capsule and suspension comprising at least one PPI and at least one immune tolerance agent in a pharmaceutically acceptable carrier designed uniquely for oral delivery of therapy to patients with recent onset type 1 diabetes, existing type 1 diabetes and Latent Autoimmune Diabetes of Adulthood. For example, Lansoprazole, a PPI, may be selected and formulated with the immune tolerance agent cyclosporine. The physical and chemical properties of Lansoprazole and cyclosporine are compatible for co-formulation in pill/capsule and oral suspension or solution form. A unit dose form of a PPI may be combined with a unit dose form of an immune tolerance agent as active pharmaceutical ingredients (APIs) in one formulated capsule and as one formulated suspension or solution.

An exemplary pharmaceutical composition of the present invention comprises 60 mg Lansoprazole and 100 mg Cyclosporine enclosed in a hard gelatin capsule with lactose as a filler. Another exemplary pharmaceutical composition of the present invention comprises 60 mg Lansoprazole, 100 mg Cyclosporine, QS to 1 ml the pharmaceutically acceptable carrier LABRASOL (Gattefosse S A), which is PEG-8 caprylic/capric glycerides, enclosed in a soft gelatin capsule. Another exemplary pharmaceutical composition of the present invention comprises 30 mg Lansoprazole, 50 mg Cyclosporine, QS to 1 ml the pharmaceutically acceptable carrier Miglyol 812N (medium chain triglycerides), enclosed in a hard gelatin capsule. Another exemplary pharmaceutical composition of the present invention comprises 60 mg Lansoprazole, 100 mg Cyclosporine, and alcohol, USP, absolute, 12.7% v/v, enclosed in a soft gelatin capsule. Another exemplary composition is an oral solution wherein each ml contains 60 mg Lansoprazole, 100 mg Cyclosporine, alcohol, Ph. Helv. 12.5% by volume dissolved in an olive oil, Ph. Helv./Labrafil M 1944 CS (polyoxyethylated oleic glycerides) vehicle which must be further diluted with milk, chocolate milk, or orange juice before oral administration. Another exemplary composition is an oral suspension wherein each ml contains 3 mg Lansoprazole and 5 mg Cyclosporine, QS to 1 ml 8.4% sodium bicarbonate (aqueous solution). Another exemplary composition is 30 mg Lansoprazole and 50 mg Cyclosporine formulated in a pill comprising pharmaceutically acceptable carriers such as fillers (e.g. saccharides, cellulose preparations and/or calcium phosphates).

In another embodiment, the invention provides a combination product comprising at least one PPI combined with another beta regeneration agent or agents inclusive but not limited to Reg Peptides, Optimized Reg Peptide formulations and/or agents that bind to the human Reg Receptor. The combination product may be used in type 1 and 2 diabetes, PreDiabetes or diseases of insulin deficiency, beta cell deficiency, insulin resistance and impaired glucose metabolism. An exemplary pharmaceutical composition of the present invention comprises 60 mg Lansoprazole, 50 mg human Reg3a peptide (HIP), and alcohol, USP, absolute, 12.8% v/v, enclosed in a soft gelatin capsule.

In another embodiment, the invention provides a combination product comprising at least one PPI combined with another beta regeneration agent or agents as a new pharmaceutical composition with one or more immune tolerance agents for usage in new onset type 1, existing type 1 diabetes and Latent Autoimmune Diabetes of Adulthood. The other beta regeneration agent(s) may include but are not limited to Reg Peptides, Optimized Reg Peptide formulations and/or agents that bind to the human Reg Receptor. Further, this invention designs a pharmaceutical composition of one PPI and one or more immune tolerance agents for insulin independence among patients with type 1 diabetes. An exemplary pharmaceutical composition of the present invention comprises 60 mg Lansoprazole, 100 mg Cyclosporine, 50 mg human Reg3a peptide (HIP), and alcohol, USP, absolute, 12.8% v/v, enclosed in a gelatin capsule.

The PPI(s) used in the compositions and methods of the present invention may include, but is not limited to Omeprazole (brand names: GASEC, LOSEC, PRILOSEC, ZEGERID, OLID, LOMAC, OMEPRAL, OMEZ), Lansoprazole (brand names: PREVACID, ZOTON, MONOLITUM, INHIBITOL, LEVANT, LUPIZOLE), Dexlansoprazole (brand name: KAPIDEX, DEXILANT), Esomeprazole (brand names: NEXIUM, ESOTREX, ESSO), Pantoprazole (brand names: PROTONIX, SOMAC, PANTOLOC, PANTOZOL, ZURCAL, ZENTRO, PAN, CONTROLOC), Rabeprazole (brand names: ACIPHEX, PARIET, ERRAZ, ZECHIN, RABECID, NZOLE-D, RABELOC, RAZO. DORAFEM) and Ilaprazole.

The immune tolerance agent(s) used in the compositions and methods of the present invention may include, but is not limited to cyclosporine, heat shock protein 60, Diapep 277, Bacille Calmette-Guérin (also known as the BCG vaccine and commonly known as the vaccine against tuberculosis), mycophenolate mofetil, daclizumab, rituximab (anti CD20), anti CD3 antibodies including hOKT3 gamma1 (Ala-Ala), and the monoclonal antibody TRX4 (ChAglyCD3), CTLA4-Ig (abatacept) a selective co-stimulation modulator as it inhibits the co-stimulation of T cells, campath-1H, anti-CD52 antibody, a humanized monoclonal antibody to T-cells, polyclonal anti-T-lymphocyte globulin (ATG), GAD antibody vaccine based on the 65 kDa isoform of the recombinant human glutamic acid decarboxylase protein (rhGAD65), diazoxide and Alpha-1 Antitrypsin.

The other beta regeneration agents used in the compositions and methods of the present invention may include but are not limited to Reg Peptides, Optimized Reg Peptide formulations and/or agents that bind to the human Reg Receptor.

Embodiments of the invention also provide kits for treating a patient having type 1 or type 2 diabetes or other condition which is associated with or is a risk factor for impaired glucose homeostasis. The kits may be used to treat patients with type 2 diabetes, PreDiabetes, glucose intolerance, hyperglycemia, syndromes of insulin resistance and glucose impairment, diseases of hyperglycemia, glucose intolerance and beta cell impairment or deficiency, insulin resistance and associated conditions including: obesity, obesity prior to the development of diabetes, obesity in children leading to PreDiabetes, childhood diabetes (both type 1 and 2) and other conditions including but not limited to polycystic ovarian syndrome, nonalcoholic steatohepatitis, hyperlipidemia and hypertriglyceridemia and other conditions related to the deficiency or lack of effective amounts of insulin. for patients with recent onset type 1 diabetes, existing type 1 diabetes and patients with Latent Autoimmune Diabetes of Adulthood.

In one embodiment, the kits of the present invention comprise one or more compositions of the present invention together with information which informs a user of the kit, by words, pictures, and/or the like, that use of the kit will treat various conditions associated with or a risk factor for impaired glucose homeostasis (e.g. type 1 or type 2 diabetes). The compositions may comprise a PPI(s) provided in a therapeutically effective dose alone or in combination with a therapeutically effective dose of another beta regeneration agent(s) including but not limited to Reg Peptides, Optimized Reg Peptides or Reg Peptide peptidomimetics and other Reg formulations. The compositions may also combine a therapeutically effective dose of a PPI(s) and/or other beta regeneration agent(s) with a therapeutically effective dosage of an immune tolerance agent(s).

In a particularly preferred embodiment, the information is printed on a container holding the composition(s), e.g., a bottle containing capsule or suspension compositions of the present invention. These preferred kits may be in the form of one bottle containing the composition(s), or may be obtained as a plurality of bottles each containing the composition(s). For example, the kits may be obtained as one bottle, or cases of four, six, seven, or eight bottles co-packaged together. The preferred kits may also include one or more dispensing means, such as in the case of where the composition is a suspension, a dispensing cap, dropper, syringe, dispensing pump, small measuring cup, or spoon, for providing a measured amount of the composition into a cup or other suitable quantity of water, juice or other beverage. The preferred kits may also include a set of instructions for dispensing and mixing the composition into a beverage.

Further embodiments provide a kit for measuring endogenous insulin, insulin-requirements, antibodies to Islet-cell autoantibodies 512 (ICA512)/islet antigen-2 (IA-2), Glutamic acid decarboxylase (GAD) autoantibodies, Insulin autoantibodies (ICA512/IA-2) at baseline and during and after treatment.

EXAMPLES

This invention describes for the first time, methods for insulin independence among new onset, existing type 1 diabetes and Latent Autoimmune Diabetes of Adulthood by the use of PPIs with immune tolerance agents, which have not previously been described in the prior art. This patent identifies new methods and pharmaceutical compositions utilizing a PPI with an immune tolerance agent for insulin independence in type 1 diabetes and LADA. The invention specifically includes the PPI, Lansoprazole dosed at 1 mg/kg/day in two divided dosages utilized with the immune tolerance agent, cyclosporine dosed at 7.5 mg/kg/day in two divided dosages for usage among recent onset and existing type 1 diabetes for insulin independence.

Once patients are begun on these two agents, glucose levels will be monitored carefully with basal insulin levels reduced by 10% when fasting glucose levels fall below 80 mg/dL. If premeal glucose levels are trending downward from baseline a 10% reduction in both the meal in which the premeal glucose level is below 100 mg/dL and the meal prior to that meal. Any symptomatic lows must be immediately reported to the physician, to appropriately lower either the basal or bolus insulin with the goal of glucose levels in the 100 mg/dL range before meals and 140 mg/dL range 2 hours after meals.

Neither Lansoprazole nor Cyclosporine have been shown to have any adverse interactions with one another. Both have physical and chemical properties providing for a pharmaceutical composition that both agents can be delivered as a single capsule or pill and single oral suspension or solution. Lansoprazole may be used alone with cyclosporine or in conjunction with other beta regeneration agents, which may include Reg peptides, derivatives, formulations and peptidomimetics to the Reg receptor.

This invention also provides methods and pharmaceutical compositions for insulin independence among 2 diabetes utilizing a PPI alone or in conjunction with a beta cell agonist including, but not limited to Reg peptides, derivatives, formulations and peptidomimetics to the Reg receptor. Once patients are begun on a PPI alone or with another beta regeneration agent, glucose levels will be monitored carefully with basal insulin levels reduced by 10% when fasting glucose levels fall below 80 mg/dL. If premeal glucose levels are trending downward from baseline a 10% reduction in both the meal in which the premeal glucose level is below 100 mg/dL and the meal prior to that meal. Any symptomatic lows must be immediately reported to the physician, to appropriately lower either the basal or bolus insulin with the goal of glucose levels in the 100 mg/dL range before meals and 140 mg/dL range 2 hours after meals.

Among type 2 patients, after insulin is tapered off, other diabetes agents including but not limited to sulfonylureas, metformin, meglitinides, GLP-1 receptor analogs, DPP-4 inhibitors, thiazolidinediones, SGLT2 inhibitors, anti-inflammatory agents and pramlintide may also be tapered as glucose levels and hemoglobin A1C fall into the normal range resulting from usage of a PPI alone or with another beta regeneration agent.

This invention also includes methods of utilizing PPIs alone or in combination with a beta cell agonist to improve glycemic control among patient with type 2 diabetes treated with diabetes medications other than insulin including, but not limited to sulfonylureas, metformin, meglitinides, GLP-1 receptor analogs, DPP-4 inhibitors, thiazolidinediones, SGLT2 inhibitors, anti-inflammatory agents and pramlintide. Once patients are begun on a PPI alone or with another beta regeneration agent, glucose levels will be monitored carefully with basal insulin levels reduced by 10% when fasting glucose levels fall below 80 mg/dL.

If premeal glucose levels are trending downward from baseline a 10% reduction in both the meal in which the premeal glucose level is below 100 mg/dL and the meal prior to that meal. Any symptomatic lows must be immediately reported to the physician, to appropriately lower either the basal or bolus insulin with the goal of glucose levels in the 100 mg/dL range before meals and 140 mg/dL range 2 hours after meals. Among type 2 patients, other diabetes agents including but not limited to sulfonylureas, metformin, meglitinides, GLP-1 receptor analogs, DPP-4 inhibitors, thiazolidinediones, SGLT2 inhibitors, anti-inflammatory agents and pramlintide may also be tapered as glucose levels and hemoglobin A1C fall into the normal range resulting from usage of a PPI alone or with another beta regeneration agent.

This invention also includes methods and pharmacologic compositions for improved glycemic control and ability to restore normoglycemic among diabetes drug naïve patients. Among a newly diagnosed or previously diagnosed 2 diabetes who is currently on no pharmaceutical treatment for diabetes, a PPI may utilized with a primary endpoint of glucose levels and Hemoglobin A1C The glucose goals would be 100 mg/dL range before meals and 140 mg/dL two hours after meals. Because there are numerous redundant mechanisms to prevent hypoglycemia, which do not allow for new beta cell formation under normal physiological conditions and even as glucose levels approach normal levels, there is limited if any ability to generate new islets, thus risk for hypoglycemia with a PPI as the only diabetic agent is limited, but as glucose levels approach normal and Hemoglobin A1C is normal, the PPI can be tapered off.

Example 1

The PPI Lansoprazole Used with Cyclosporine for Insulin Independence Among Type 1 Diabetes Patients The combination of an immune tolerance agent (e.g. Cyclosporine initially dosed at 7.5 mg/kg/day in divided dosages at breakfast and dinner and based on peak and trough levels, the dosage will be modified to optimize immune tolerance and limit side effects) with Lansoprazole dosed at 30 mg per day given in two divided (15 mg per dosage) for children less than 11 years old weighing 66 pounds or less. For children older than 11 years and weighing more than 66 pounds Lansoprozole, will be dosed as 60 mg per day given in two divided dosage of 30 mg each and may be delivered in one capsule/pill or in one suspension per dosage to results in insulin independence. For adults, Lansoprazole will be given as 60 mg twice daily by mouth in pill or oral suspension. Exogenous insulin dosages, whether by injection or pump, are decreased and able to be tapered off based upon glucose levels before meals and fasting. Modifications made in lowering insulin, will be made based on whether the patient demonstrates high or low fasting glucose levels, commonly impacted by a basal insulin vs. the patient having high or low pre-meal glucose levels, which may likely reflect the dosing of insulin at the prior meal, whereas, the 2-hour postprandial glucose levels reflects the insulin given prior to the meal.

Example 2

The PPI Lansoprazole Used for Insulin Independence Among Type 2 Diabetes

Thirty milligrams of Lansoprazole per day given will be given in two divided (15 mg per dosage) for children less than 11 years old weighing 66 pounds or less, and for children older than 11 years and weighing more than 66 pounds, Lansoprozole will be dosed as 60 mg per day given in two divided dosage of 30 mg each and may be delivered in one capsule/pill or in one suspension per dosage to results in insulin independence. For adults, Lansoprazole will be given as 60 mg twice daily by mouth in pill or oral suspension resulting in insulin independence. Exogenous insulin dosages, whether by injection or pump are decreased based on glucose levels before meals and fasting. Exogenous insulin dosages, whether by injection or pump, are decreased and able to be tapered off based upon glucose levels before meals and fasting. Modifications made in lowering insulin, will be made based on whether the patient demonstrates high or low fasting glucose levels, commonly impacted by a basal insulin vs. the patient having high or low pre-meal glucose levels, which may likely reflect the dosing of insulin at the prior meal, whereas, the 2-hour postprandial glucose levels reflects the insulin given prior to the meal.

Based upon glucose levels, other diabetes agents such as sulfonylureas, metformin, meglitinides, GLP-1 receptor analogs, DPP-4 inhibitors, thiazolidinediones, SGLT2 inhibitors, anti-inflammatory agents and pramlintide may also be tapered based on glucose levels and hemoglobin A1C. Metformin, thiazolidinediones, SGLT2 inhibitors work as basal glucose lowering agents, whereas, sulfonylureas, GLP-1 receptor analogs, DPP-4 inhibitors, meglitinides work to reduce postprandial glucose levels, thus modifications made in lowering these agents will be based on whether the patient demonstrates high or low fasting glucose levels, commonly impacted by a basal agent vs. the patient has high or low pre-meal glucose levels, which may likely reflect under dosing of a diabetes medication prior to the previous meal.

Example 3

The PPI Lansoprazole Used for Reducing Diabetes Medications Requirements Among Type 2 Diabetes Lansoprazole will be dosed at 30 mg per day given in two divided (15 mg per dosage) for children less than 11 years old weighing 66 pounds or less, and for children older than 11 years and weighing more than 66 pounds Lansoprozole will be dosed as 60 mg per day given in two divided dosage of 30 mg each and may be delivered in one capsule/pill or in one suspension per dosage to results in insulin independence. For adults, Lansoprazole will be given as 60 mg twice daily by mouth in pill or oral suspension. Lansoprazole given in divided dosages in one capsule/pill or in on oral suspension may result in the need to diminish dosages of other diabetes medications utilized and such medications may potentially be tapered off. Medications include: sulfonylureas, metformin, meglitinides, GLP-1 receptor analogs, DPP-4 inhibitors, thiazolidinediones, SGLT2 inhibitors, anti-inflammatory agents and pramlintide may also be tapered based on glucose levels and hemoglobin A1C. Metformin, thiazolidinediones, SGLT2 inhibitors work as basal glucose lowering agents, whereas, sulfonylureas, GLP-1 receptor analogs, DPP-4 inhibitors, meglitinides work to reduce postprandial glucose levels, thus modifications made in lowering these agents will be based on whether the patient demonstrates high or low fasting glucose levels, commonly impacted by a basal agent vs. the patient has high or low pre-meal glucose levels, which may likely reflect under dosing of a diabetes medication prior to the previous meal. Modifications made to the diabetes medication regimen will be made based on whether the patient glucose levels and the need to adjust the basal or postprandial agent will be made.

Example 4

The PPI Lansprazole Used for Drug Naive Type 2 Diabetes

Lansoprazole dosed at 30 mg per day given in two divided (15 mg per dosage) for children less than 11 years old weighing 66 pounds or less. For children older than 11 years and weighing more than 66 pounds, Lansoprozole will be dosed as 60 mg per day given in two divided dosage of 30 mg each and may be delivered in one capsule/pill or in one suspension per dosage to results in insulin independence. For adults, Lansoprazole will be given as 60 mg twice daily by mouth in pill or oral suspension. Lansoprazole given in divided dosages in one capsule/pill or in on oral suspension results in normalization of blood glucose as measured by fasting glucose and hemoglobin A1C levels. Among a newly diagnosed or previously diagnosed 2 diabetes who is currently on no pharmaceutical treatment for diabetes, a PPI (example Lansoprazole dosed from 30-120 mg daily in two divided dosages) is utilized to assess the safety and efficacy among patients with type 2 diabetes with a primary endpoint of glucose levels and Hemoglobin A1C in the normal range and secondary endpoints of diabetes medication requirements and stimulated C-peptide (under the curve). The glucose goals would be 100 mg/dL range before meals and 140 mg/dL two hours after meals.

Example 5

The Use of PPI Lansoprazole is Used for Ex Vivo Generation of Beta Cells and Provided to Patients with Labile Type 1 and Type 2 Diabetes with Cyclosporine for Insulin Independence A PPI alone or in combination with other beta regeneration agents, which may include but are not limited to Reg Peptides, Optimized Reg Peptide formulations and/or agents that bind to the human Reg Receptor are used for the ex vivo transformation of new beta cells from pluripotent stem cells including embryonic cells, adult somatic stem cells, human adult bone-marrow derived stem cells, umbilical cord stems cells, mesenchymal stem cells, human amniotic membrane-derived mesenchymal cells, mammalian stem cells, mammalian stem cells, ectodermal stem cells or other stem cells and may include resident populations of endogenous stem cells that exist within the adult pancreas. The new beta cells are then administered to patients with new and existing type 1 and 2 diabetes, PreDiabetes or diseases of insulin deficiency, beta cell deficiency, insulin resistance and impaired glucose metabolism, with routes of delivery to include, but are not limited to the portal and umbilical vein, oral, intravenous, subcutaneous delivery with and without organ specific targeting and may include direct administration to the pancreas or liver. Patients receiving ex vivo formulated beta cells will require an immune tolerance agent to prevent autoimmune attack of the newly received beta cells. For example, patients will receive 7.5 mg/kg/day of cyclosporine in divided dosages prior to receiving the ex vivo generated beta cells with dosages of cyclosporine adjusted based upon peak and trough levels to optimize efficacy and reduce risks of side effects.

Example 6

The PPI Pantoprazole Used with Cyclosporine for Insulin Independence Among Type 1 Diabetes Patients The combination of an immune tolerance agent (e.g. Cyclosporine initially dosed at 7.5 mg/kg/day in divided dosages at breakfast and dinner and based on peak and trough levels, the dosage will be modified to optimize immune tolerance and limit side effects) with 40 mg of Pantoprazole given in twice daily (among adults) in one oral capsule/pill or in one oral suspension results in insulin independence. Among children aged five years and older, the dosage Pantoprazole is given with cyclosporine is 10 mg twice daily for children between 33 and 87 pounds and children above 87 pounds will be given 20 mg twice daily of Pantoprazole with cyclosporine.

Example 7

The PPI Pantoprazole Used for Insulin Independence Among Type 2 Diabetes

Forty mg given twice daily of Pantoprazole is given in an oral capsule/pill or suspension formulation results in insulin independence in adults and among children, 10-20 mg of Pantoprazole is given twice daily depending on weight with 10 mg twice daily being given to children between 33 and 87 pounds and children above 87 pounds being given 20 mg twice daily of Pantoprazole for insulin independence. Exogenous insulin dosages, whether by injection or pump are decreased based on glucose levels before meals and fasting. Exogenous insulin dosages, whether by injection or pump, are decreased and able to be tapered off based upon glucose levels before meals and fasting. Modifications made in lowering insulin, will be made based on whether the patient demonstrates high or low fasting glucose levels, commonly impacted by a basal insulin vs. the patient having high or low pre-meal glucose levels, which may likely reflect the dosing of insulin at the prior meal, whereas, the 2-hour postprandial glucose levels reflects the insulin given prior to the meal.

Based upon glucose levels, other diabetes agents such as sulfonylureas, metformin, meglitinides, GLP-1 receptor analogs, DPP-4 inhibitors, thiazolidinediones, SGLT2 inhibitors, anti-inflammatory agents and pramlintide may also be tapered based on glucose levels and hemoglobin A1C. Metformin, thiazolidinediones, SGLT2 inhibitors work as basal glucose lowering agents, whereas, sulfonylureas, GLP-1 receptor analogs, DPP-4 inhibitors, meglitinides work to reduce postprandial glucose levels, thus modifications made in lowering these agents will be based on whether the patient demonstrates high or low fasting glucose levels, commonly impacted by a basal agent vs. the patient has high or low pre-meal glucose levels, which may likely reflect under dosing of a diabetes medication prior to the previous meal.

Example 8

The PPI Pantoprazole Used for Reducing Diabetes Medications Requirements Among Type 2 Diabetes Pantoprazole is given twice daily (among adults) in one oral capsule/pill or in one oral suspension results in insulin independence. Among children aged five years and older, the dosage Pantoprazole of 10 mg twice daily for children between 33 and 87 pounds and children above 87 pounds will be given 20 mg twice daily of Pantoprazole in one capsule/pill or in one oral suspension resulting in the need to diminish dosages of other diabetes medications utilized and such medications may potentially be tapered off. Medications include: sulfonylureas, metformin, meglitinides, GLP-1 receptor analogs, DPP-4 inhibitors, thiazolidinediones, SGLT2 inhibitors, anti-inflammatory agents and pramlintide may also be tapered based on glucose levels and hemoglobin A1C. Metformin, thiazolidinediones, SGLT2 inhibitors work as basal glucose lowering agents, whereas, sulfonylureas, GLP-1 receptor analogs, DPP-4 inhibitors, meglitinides work to reduce postprandial glucose levels, thus modifications made in lowering these agents will be based on whether the patient demonstrates high or low fasting glucose levels, commonly impacted by a basal agent vs. the patient has high or low pre-meal glucose levels, which may likely reflect under dosing of a diabetes medication prior to the previous meal. Modifications made to the diabetes medication regimen will be made based on whether the patient glucose levels and the need to adjust the basal or postprandial agent will be made.

Example 9

The PPI Pantoprazole Used for Drug Naive Type 2 Diabetes

Pantoprazole is given in twice daily (among adults) in one oral capsule/pill or in one oral suspension for patients with type 2 diabetes. Among children aged five years and older, the dosage pantoprazole is given with cyclosporine is 10 mg twice daily for children between 33 and 87 pounds and children above 87 pounds will be given 20 mg twice daily of pantoprazole in one capsule/pill or in on oral suspension results in normalization of blood glucose as measured by fasting glucose and hemoglobin A1C levels. Among a newly diagnosed or previously diagnosed 2 diabetes who is currently on no pharmaceutical treatment for diabetes, a PPI (example: Pantoprazole in 10, 20 or 40 mg twice daily) is utilized to assess the safety and efficacy among patients with type 2 diabetes with a primary endpoint of glucose levels and Hemoglobin A1C in the normal range and secondary endpoints of diabetes medication requirements and stimulated C-peptide (under the curve). The glucose goals would be 100 mg/dL range before meals and 140 mg/dL two hours after meals.

Example 10

The Use of PPI Pantoprazole is Used for Ex Vivo Generation of Beta Cells and Provided to Patients with Labile Type 1 and Type 2 Diabetes with Cyclosporine for Insulin Independence A PPI (such as Pantoprazole) is used alone or in combination with other beta regeneration agents, which may include but are not limited to Reg Peptides, Optimized Reg Peptide formulations and/or agents that bind to the human Reg Receptor are used for the ex vivo transformation of new beta cells from pluripotent stem cells including embryonic cells, adult somatic stem cells, human adult bone-marrow derived stem cells, umbilical cord stems cells, mesenchymal stem cells, human amniotic membrane-derived mesenchymal cells, mammalian stem cells, mammalian stem cells, ectodermal stem cells or other stem cells and may include resident populations of endogenous stem cells that exist within the adult pancreas. The new beta cells are then administered to patients with new and existing type 1 and 2 diabetes, PreDiabetes or diseases of insulin deficiency, beta cell deficiency, insulin resistance and impaired glucose metabolism, with routes of delivery to include, but are not limited to the portal and umbilical vein, oral, intravenous, subcutaneous delivery with and without organ specific targeting and may include direct administration to the pancreas or liver. Patients receiving ex vivo formulated beta cells will require an immune tolerance agent to prevent autoimmune attack of the newly received beta cells. For example, patients will receive 7.5 mg/kg/day of cyclosporine in divided dosages prior to receiving the ex vivo generated beta cells with dosages of cyclosporine adjusted based upon peak and trough levels to optimize efficacy and reduce risks of side effects.

Exogenous insulin dosages, whether by injection or pump, are decreased and able to be tapered off based upon glucose levels before meals and fasting. Modifications made in lowering insulin, will be made based on whether the patient demonstrates high or low fasting glucose levels, commonly impacted by a basal insulin vs. the patient having high or low pre-meal glucose levels, which may likely reflect the dosing of insulin at the prior meal, whereas, the 2-hour postprandial glucose levels reflects the insulin given prior to the meal.

ADDITIONAL EMBODIMENTS

Embodiment 1x

A method of treating a condition that is associated with or is a risk factor for impaired glucose homeostasis in a subject selected from new onset type 1 and 2 diabetes, previously existing type 1 and 2 diabetes, latent autoimmune diabetes of adulthood (LADA), glutamic acid decarboxylase-65 autoimmunity, prediabetes, hyperglycemia, glucose intolerance, beta cell impairment or deficiency, insulin resistance, obesity, polycystic ovarian syndrome, nonalcoholic steatohepatitis, hyperlipidemia, and hypertriglyceridemia, comprising the step of:
administering an amount of a proton pump inhibitor to the subject that is effective for generating new beta cells in the pancreas of the subject and/or reducing or preventing symptoms of the condition.

Embodiment 2x

The method of embodiment 1x, further comprising the step of administering an amount of an immune tolerance agent to the subject that is effective for protecting the new beta cells from destruction from the immune system and/or reducing or preventing symptoms of the condition.

Embodiment 3x

The method of embodiment 1x, further comprising the step of administering an amount of at least one other beta regeneration agent that is effective for generating new beta cells in the pancreas of the subject and/or reducing or preventing symptoms of the condition.

Embodiment 4x

The method of embodiment 2x, further comprising the step of administering an amount of at least one other beta regeneration agent that is effective for generating new beta cells in the pancreas of the subject and/or reducing or preventing symptoms of the condition.

Embodiment 5x

The method of embodiment 1x, wherein the proton pump inhibitor is selected from Omeprazole, Lansoprazole, Dexlansoprazole, Esomeprazole, Pantoprazole, Rabeprazole, and Ilaprazole.

Embodiment 6x

The method of embodiment 2x, wherein the immune tolerance agent is selected from Cyclosporine, hOKT3γ1, ChAglyCD3, Rapamycin, Tacrolimus, Etanercept, Alefacept, Belatacept, Diapep277, a tuberculosis vaccine, Glutamic Acid Decarboxylase 65 (GAD65) vaccine; Bacillus Calmette-Guérin Vaccine, Mycophenolate Mofetil alone or in combination with Daclizumab; Rituximab; Campath-1H, lysofylline; antithymocyte globulin, Proleukin and the combination of Proleukin and Rapamune, Vitamin D, IBC-VSO vaccine, Ex vivo Expanded Human Autologous CD4+ CD127lo/–CD25+ Polyclonal Regulatory T Cells; interferon-alpha; a vaccine using $CD4^+CD25^+$ antigen-specific regulatory T cells, Interleukin-1 Receptor Antagonist (anakinra), and Alpha 1-Antitrypsin.

Embodiment 7x

The method of embodiment 3x, wherein the other beta regeneration agent is a Reg Peptide, or a formulation, derivative, optimized form or peptidomimetic of a Reg Peptide.

Embodiment 8x

The method of embodiment 4x, wherein the other beta regeneration agent is a Reg Peptide, or a formulation, derivative, optimized form or peptidomimetic of a Reg Peptide.

Embodiment 9x

The method of embodiment 2x, wherein the proton pump inhibitor is Lansoprazole.

Embodiment 10x

The method of embodiment 2x, wherein the immune tolerance agent is Cyclosporine.

Embodiment 11x

The method of embodiment 2x, wherein the proton pump inhibitor and the immune tolerance agent are formulated together in a pharmaceutical composition.

Embodiment 12x

The method of embodiment 11x, wherein the proton pump inhibitor is Lansoprazole.

Embodiment 13x

The method of embodiment 11x, wherein the immune tolerance agent is Cyclosporine.

Embodiment 14x

The method of embodiment 11x, wherein the proton pump inhibitor is Lansoprazole and the immune tolerance agent is Cyclosporine.

Embodiment 15x

The method of embodiment 14x, wherein Lansoprazole and Cyclosporine are formulated together in a capsule, pill, suspension, or solution.

Embodiment 16x

The method of embodiment 15x, wherein Lansoprazole and Cyclosporine are administered orally.

Embodiment 17x

The method of embodiment 2x, wherein the condition that is associated with impaired glucose homeostasis is type 1 diabetes or latent autoimmune diabetes of adulthood (LADA).

Embodiment 18x

The method of embodiment 17x, wherein treatment results in reduction in diabetes medication requirements.

Embodiment 19x

The method of embodiment 18x, wherein the diabetes medication is insulin.

Embodiment 20x

The method of embodiment 19x, wherein the treatment results in insulin independence.

Embodiment 21x

The method of embodiment 17x, wherein the proton pump inhibitor is Lansoprazole and the immune tolerance agent is Cyclosporine.

Embodiment 22x

The method of embodiment 1x, wherein the condition that is associated with impaired glucose homeostasis is type 1 diabetes.

Embodiment 23x

The method of embodiment 1x, wherein the condition that is associated with impaired glucose homeostasis is type 2 diabetes.

Embodiment 24x

The method of embodiment 23x, wherein the subject is diabetes-drug naïve.

Embodiment 25x

The method of embodiment 23x, wherein the subject has been exposed to and requires diabetes medications.

Embodiment 26x

The method of embodiment 25x, wherein treatment results in reduction in diabetes medication requirements.

Embodiment 27x

The method of embodiment 25x, wherein the diabetes medication is insulin.

Embodiment 28x

The method of embodiment 26x, wherein the diabetes medication is insulin.

Embodiment 29x

The method of embodiment 28x, wherein the treatment results in insulin independence.

Embodiment 30x

The method of embodiment 23x, wherein the proton pump inhibitor is Lansprazole.

Embodiment 31x

The method of embodiment of embodiment 1x, wherein the condition that is associated with impaired glucose homeostasis is PreDiabetes.

Embodiment 32x

The method of embodiment 2x, wherein the condition that is associated with impaired glucose homeostasis is type 2 diabetes.

Embodiment 33x

A method for treating a pathology associated specifically with impaired pancreatic function in a subject comprising the step of:
administering a therapeutically effective amount of a proton pump inhibitor to the subject.

Embodiment 34x

The method of embodiment 33x, further comprising the step of administering a therapeutically effective amount of an immune tolerance agent to the subject.

Embodiment 35x

The method of embodiment 34x, further comprising one or more steps of:
(a) intensifying glycemic control;
(b) administering oral vitamin D to maintain 25-hydroxyvitamin levels above 40 mg/ml;
(c) reducing, or tapering off of other diabetes therapies as new beta cell populations are restored;
(d) lowering the dosage of the immune tolerance agent and the PPI as dosages of other diabetes medication, including insulin, are tapered off; and
(e) administering the lowest dosage formulations of PPIs alone and in combination with immune tolerance agents at intervals to maintain a minimum number of beta cells for normal glucose metabolism.

Embodiment 36x

The method of embodiment 35x, wherein the pathology associated specifically with impaired pancreatic function is type 1 diabetes.

Embodiment 37x

A method of treating recent and existing type 1 diabetes in a subject comprising the step of administering Cyclosporine and another diabetes agent.

Embodiment 1y

A method for the generation of new beta cells from extra-islet ductal tissue or pluripotent stem cells, comprising the steps of:
a. culturing the extra-islet ductal tissue or pluripotent stem cells ex vivo; and
b. contacting said extra-islet ductal tissue or pluripotent stem cells with a proton pump inhibitor, wherein the amount of proton pump inhibitor is effective for forming beta cells from said extra-islet ductal tissue or pluripotent stem cells.

Embodiment 2y

The method of embodiment 1y, further comprising the step of contacting said extra-islet ductal tissue or pluripotent stem cells with at least one other beta regeneration agent.

Embodiment 3y

The method of embodiment 1y, wherein the pluripotent stem cells are embryonic cells, adult somatic stem cells, human adult bone-marrow derived stem cells, umbilical cord stems cells, mesenchymal stem cells, human amniotic membrane-derived mesenchymal cells, mammalian stem cells, ectodermal stem cells, or endogenous stem cells that exist within the adult pancreas.

Embodiment 4y

The method of embodiment 2y, wherein the other beta regeneration agent is a Reg Peptide, or a formulation, derivative, optimized form or peptidomimetic of a Reg Peptide.

Embodiment 5y

A method of treating a condition that is associated with or is a risk factor for impaired glucose homeostasis in a subject selected from new onset type 1 and 2 diabetes, previously existing type 1 and 2 diabetes, latent autoimmune diabetes of adulthood (LADA), glutamic acid decarboxylase-65 autoimmunity, prediabetes, hyperglycemia, glucose intolerance, beta cell impairment or deficiency, insulin resistance, obesity, polycystic ovarian syndrome, nonalcoholic steatohepatitis, hyperlipidemia, and hypertriglyceridemia, comprising the steps of:
a. culturing the extra-islet ductal tissue or pluripotent stem cells ex vivo; and
b. contacting said extra-islet ductal tissue or pluripotent stem cells with a proton pump inhibitor, wherein the amount of proton pump inhibitor is effective for forming beta cells from said extra-islet ductal tissue or pluripotent stem cells.
c. administering the beta cells to the subject.

Embodiment 6y

The method of embodiment 5y, further comprising the step of contacting said extra-islet ductal tissue or pluripotent stem cells with another beta regeneration agent, wherein the amount of other beta regeneration agent is effective for forming beta cells.

Embodiment 7y

The method of embodiment 5y, wherein the pluripotent stem cells are embryonic cells, adult somatic stem cells, human adult bone-marrow derived stem cells, umbilical cord stems cells, mesenchymal stem cells, human amniotic membrane-derived mesenchymal cells, mammalian stem cells, ectodermal stem cells, or endogenous stem cells that exist within the adult pancreas.

Embodiment 8y

The method of embodiment 6y, wherein the other beta regeneration agent is a Reg Peptide, or a formulation, derivative, optimized form or peptidomimetic of a Reg Peptide.

Embodiment 9y

The method of embodiment 5y, wherein the beta cells are administered to the subject through an oral, intravenous, subcutaneous, or intra-arterial route of administration.

Embodiment 10y

The method of embodiment 5y, wherein the beta cells are delivered through the umbilical vein, portal vein, or hepatic artery.

Embodiment 11y

The method of embodiment 5y, wherein the beta cells are delivered directly to the pancreas or the liver.

Embodiment 12y

The method of embodiment 5y, wherein the condition is new and existing type 1 and 2 diabetes, prediabetes, beta cell deficiency, insulin resistance or impaired glucose metabolism.

Embodiment 13y

The method of embodiment 5y, wherein the condition is associated with autoimmunity and an immune tolerance agent is administered before and/or in parallel with the administration of the beta cells.

Embodiment 14y

The method of embodiment 13y, wherein the condition is type 1 diabetes or LADA.

Embodiment 15y

The method of embodiment 13y, wherein the immune tolerance agent is selected from Cyclosporine, hOKT3γ1, ChAglyCD3, Rapamycin, Tacrolimus, Etanercept, Alefacept, Belatacept, Diapep277, a tuberculosis vaccine, Glutamic Acid Decarboxylase 65 (GAD65) vaccine; Bacillus Calmette-Guírin Vaccine, Mycophenolate Mofetil alone or in combination with Daclizumab; Rituximab; Campath-1H, lysofylline; antithymocyte globulin, Proleukin and the combination of Proleukin and Rapamune, Vitamin D, IBC-VSO vaccine, Ex vivo Expanded Human Autologous CD4+CD127lo/−CD25+ Polyclonal Regulatory T Cells; interferon-alpha; a vaccine using CD4+CD25$^+$ antigen-specific regulatory T cells, Interleukin-1 Receptor Antagonist (anakinra), and Alpha 1-Antitrypsin.

Embodiment 16y

The method of embodiment 13y, wherein the immune tolerance agent is Cyclosporine.

Embodiment 17y

The method of embodiment 5y, wherein a PPI or at least one other beta regeneration agent or both are administered to the subject to accelerate the formation of new beta cells in the subject.

Embodiment 18y

The method of embodiment 17y, where the condition is prediabetes or new onset or pre-existing type 2 diabetes.

Embodiment 19y

The method of embodiment 18y, wherein the subject is diabetes drug naïve.

Embodiment 1z

A pharmaceutical composition comprising a proton pump inhibitor and an immune tolerance agent.

Embodiment 2z

The composition of embodiment 1z, further comprising a pharmaceutically acceptable carrier.

Embodiment 3z

The composition of embodiment 1z, wherein the proton pump inhibitor is selected from Omeprazole, Lansoprazole, Dexlansoprazole, Esomeprazole, Pantoprazole, Rabeprazole, and Ilaprazole.

Embodiment 4z

The composition of embodiment 1z, wherein the immune tolerance agent is selected from Cyclosporine, hOKT3γ1, ChAglyCD3, Rapamycin, Tacrolimus, Etanercept, Alefacept, Belatacept, Diapep277, a tuberculosis vaccine, Glutamic Acid Decarboxylase 65 (GAD65) vaccine; Bacillus Calmette-Guérin Vaccine, Mycophenolate Mofetil alone or in combination with Daclizumab; Rituximab; Campath-1H, lysofylline; antithymocyte globulin, Proleukin and the combination of Proleukin and Rapamune, Vitamin D, IBC-VSO vaccine, Ex vivo Expanded Human Autologous CD4+CD127lo/−CD25+ Polyclonal Regulatory T Cells; interferon-alpha; a vaccine using CD4$^+$CD25$^+$ antigen-specific regulatory T cells, Interleukin-1 Receptor Antagonist (anakinra), and Alpha 1-Antitrypsin.

Embodiment 5z

The composition of embodiment 1z, wherein the proton inhibitor is Lansoprazole.

Embodiment 6z

The composition of embodiment 1z, wherein the immune tolerance agent is Cyclosporine.

Embodiment 7z

The composition of embodiment 1z, wherein the proton pump inhibitor is Lansoprazole and the immune tolerance agent is Cyclosporine.

Embodiment 8z

The composition of embodiment 1z, wherein the composition is formulated in a pill.

Embodiment 9z

The composition of embodiment 1z, wherein the composition is formulated in a capsule.

Embodiment 10z

The composition of embodiment 1z, wherein the composition is formulated in a solution or suspension.

Embodiment 11z

The composition of embodiment 7z, wherein the composition is formulated in a pill.

Embodiment 12z

The composition of embodiment 7z, wherein the composition is formulated in a capsule.

Embodiment 13z

The composition of embodiment 7z, wherein the composition is formulated in a solution or suspension.

Embodiment 14z

The composition of embodiment 8z, wherein the proton pump inhibitor and immune tolerance agent are combined in unit dose forms.

Embodiment 15z

The composition of embodiment 9z, wherein the proton pump inhibitor and immune tolerance agent are combined in unit dose forms.

Embodiment 16z

The composition of embodiment 10z, wherein the proton pump inhibitor and immune tolerance agent are combined in unit dose forms.

Embodiment 17z

The composition of embodiment 11z, wherein Lansoprazole and Cyclosporin are combined in unit dose forms.

Embodiment 18z

The composition of embodiment 12z, wherein Lansoprazole and Cyclosporin are combined in unit dose forms.

Embodiment 19z

The composition of embodiment 13z, wherein Lansoprazole and Cyclosporin are combined in unit dose forms.

Embodiment 20z

The composition of embodiment 1z, further comprising at least one other beta regeneration agent.

Embodiment 21z

The composition of embodiment 20z, wherein the other beta regeneration agent is a Reg Peptide, or a formulation, derivative, optimized form or peptidomimetic of a Reg Peptide.

Embodiment 22z

A kit comprising the composition of embodiment 1z.

Embodiment 23z

A kit comprising the composition of embodiment 20z.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

I claim:

1. A method of treating a condition that is associated with impaired glucose homeostasis in a subject, the method comprising:
culturing pancreatic extra-islet ductal tissue ex vivo;
contacting the pancreatic extra-islet ductal tissue with a proton pump inhibitor, wherein the amount of proton pump inhibitor is effective for forming beta cells from the pancreatic extra-islet ductal tissue in culture; and
administering the beta cells to the subject.

2. The method of claim 1, further comprising contacting the pancreatic extra-islet ductal tissue with an additional beta regeneration agent, wherein the amount of the additional beta regeneration agent is effective for forming beta cells.

3. The method of claim 2, wherein the additional beta regeneration agent is a Reg Peptide, or a formulation or peptidomimetic of a Reg Peptide.

4. The method of claim 1, wherein the beta cells are administered to the subject through an oral, intravenous, subcutaneous, or intra-arterial route of administration.

5. The method of claim 1, wherein the beta cells are delivered through the umbilical vein, portal vein, or hepatic artery.

6. The method of claim 1, wherein the beta cells are delivered directly to the pancreas or the liver.

7. The method of claim 1, wherein the condition that is associated with impaired glucose homeostasis is new and existing type 1 and 2 diabetes, prediabetes, beta cell deficiency, insulin resistance or impaired glucose metabolism.

8. The method of claim 1, wherein the condition that is associated with impaired glucose homeostasis is associated with autoimmunity and an immune tolerance agent is administered before and/or in parallel with the administration of the beta cells.

9. The method of claim 8, wherein the condition that is associated with impaired glucose homeostasis is type 1 diabetes or LADA.

10. The method of claim 8, wherein the immune tolerance agent is selected from Cyclosporine, hOKT3γ1, ChAglyCD3, Rapamycin, Tacrolimus, Etanercept, Alefacept, Belatacept, Diapep277, a tuberculosis vaccine, Glutamic Acid Decarboxylase 65 (GAD65) vaccine; Bacillus Calmette-Guérin Vaccine, Mycophenolate Mofetil alone or in combination with Daclizumab; Rituximab; Campath-1H, lysofylline; anti-thymocyte globulin, Proleukin and the combination of Proleukin and Rapamune, Vitamin D, IBC-VSO vaccine, Ex vivo Expanded Human Autologous CD4+CD127lo/−CD25+ Polyclonal Regulatory T Cells; interferon-alpha; a vaccine using CD4$^+$CD25$^+$ antigen-specific regulatory T cells, Interleukin-1 Receptor Antagonist (anakinra), and Alpha 1-Antitrypsin.

11. The method of claim 8, wherein the immune tolerance agent is Cyclosporine.

12. The method of claim 1, further comprising administration of a PPI or at least one other beta regeneration agent or both to the subject to stimulate formation of new beta cells in the subject in vivo.

13. The method of claim 12, where the condition that is associated with impaired glucose homeostasis is prediabetes or new onset or pre-existing type 2 diabetes.

14. The method of claim 13, wherein the subject is diabetes drug naïve.

* * * * *